US005621180A

United States Patent [19]
Simon et al.

[11] Patent Number: 5,621,180
[45] Date of Patent: Apr. 15, 1997

[54] CAPILLARY SAMPLING FLOW CONTROLLER

[75] Inventors: Philippe Simon, Montréal; Jean-Pierre Farant, Verdun, both of Canada

[73] Assignee: Martinex R & D Inc., Montreal, Canada

[21] Appl. No.: 646,073

[22] Filed: May 7, 1996

[30] Foreign Application Priority Data

May 11, 1995 [GB] United Kingdom ............... 9509577

[51] Int. Cl.$^6$ ................................................. G01N 1/24
[52] U.S. Cl. ................................ 73/804.52; 73/863.01; 73/863.23
[58] Field of Search ........................ 73/863.01, 863.23, 73/864.34, 864.51, 864.52, 864.91, 864.73

[56] References Cited

U.S. PATENT DOCUMENTS

| | | | |
|---|---|---|---|
| 3,410,059 | 11/1968 | Garnier | 73/864.34 |
| 3,618,822 | 11/1971 | Hildenbrandt, Jr. | |
| 4,040,299 | 8/1977 | Snyder | 73/864.52 |
| 4,455,881 | 5/1984 | Clark et al. | 73/864.52 |
| 4,456,014 | 6/1984 | Buck et al. | |
| 4,776,208 | 10/1988 | Dimoff | |

OTHER PUBLICATIONS

American Heritage Dictionary, Def. of "phenomenology".
NRL Report 7963, Personal Atmospheric Gas Sampler with a Critical Orifice, Part 1—Development and Evaluation—Eaton et al, Feb. 13, 1976.
MDA Scientific, Inc. Feb. 1978, Critical Orifice Personal Sampler.
Rasmussen—At Last!, A Constant–Lowrate Flow Controller for 24–Hour Passive Sampling with 6–L Summa Cans, May 16, 1995.
Millaflow brochure SC420 series Flow Controller.
Air Toxics Ltd. Brochure, Air Toxics' Guide to Air Sampling and Analysis. vol. I, Canisters and Tedlar Bags.
Canada 1,275,231 (Derwent Abstract).
Australia 9345478 (Derwent Abstract).
SU 1145267 (Derwent Abstract).
US 4456014 (Derwent Abstract).
DE 3208320 (Derwent Abstract).

*Primary Examiner*—Robert Raevis
*Attorney, Agent, or Firm*—Swabey Ogilvy Renault

[57] ABSTRACT

A capillary sampling flow controller provides an improvement in the process of sampling or monitoring for the analysis of air and gas chemistries; a constant flow rate is used to introduce a specific volume of gas into a vessel or through a trapping media over the selected sampling period. The improvement employs calculated geometry of the capillaries employed to deliver the gas sample to the evacuated vessel. It can also include a pressure reading device installed between the vessel and the capillary, and a filter at the inlet. The length of capillary with available internal diameters is estimated mathematically and confirmed experimentally to achieve any sampling time using any size sampler. The flow rate obtained from the controller is constant over its operating range and is designed to meet a specific sampling duration to obtain long-term integrated samples. The sampling process becomes completely passive, precise, reliable and simple to operate.

17 Claims, 18 Drawing Sheets

FIG_2

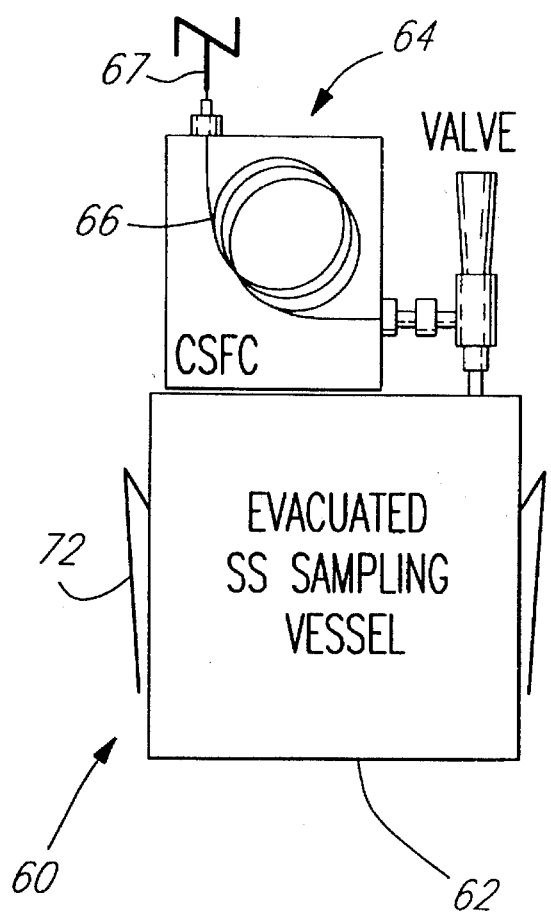
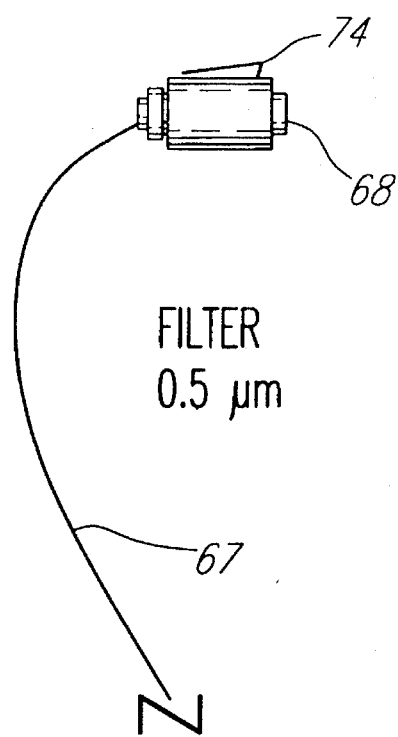
FIG. 3

FIG_6

FIG_12

FIG_15

CAPILLARY SAMPLING FLOW CONTROLLER

BACKGROUND OF THE INVENTION i) Field of the Invention

This invention relates to the collection of gases or ambient air samples. More specifically, the invention relates to a novel flow controller wherein calculated dimensions of a capillary tube are used to introduce a constant flow of sample into any size of pre-evacuated sampling vessel. Any flow rate is theoretically possible and hence, choices of average sampling time can be selected. The time integration property of this new flow controller is a major attribute. It can contribute in extending sampling duration to obtain more relevant data on the mean levels of contaminants. Also, it can be used to collect grab samples and short term sampling can efficiently be controlled. It provides benefits in air quality studies and process control monitoring.

ii) Description of Prior Art

In air quality monitoring, the sampling methodology is a critical step where many requirements must be fulfilled to assure reliability and to optimize precision prior to the laboratory analytical determination. For many target chemicals, regulations are applied in the workplace to mitigate potential health hazards from inhalation. Again, many chemicals are also regulated in the environment considering their local or global effects. For an industrial hygienist or an environmentalist, active methods of ambient air sampling are mostly used such as sampling pumps and sorbent tubes, to characterize the risk and/or to verify compliance.

At present, active sampling devices consist of cumbersome and expensive equipment that can efficiently collect at best only 24-hour integrated samples. With these existing methodologies, the sampling duration is limited by technological considerations for the achievement of low and precise flow rate. Sample size is also reduced when the investment in equipment required for an extensive field study is considered.

In the case of gaseous contaminants such as organic vapors, all present sampling methodologies have an upper integrative time boundary. According to the sampling principles applied in workplace monitoring employing sorbent cartridges, it is still difficult to adequately characterize the nature of mean exposures. Such methods require that enough air be collected at a definite flow rate to assure the validity of laboratory analysis (adequate amount of trapped analytes vs analytical limits of detection).

In order to simplify the sampling procedures and lower the cost of air quality studies, passive techniques have been developed but they lack either precision or versatility. For the measurement of volatile organic compounds in air, a sampling procedure has been developed recently by the U.S. Environmental Protective Agency using a pre-evacuated stainless steel vessel or Summa (Trade Mark) canister as a whole air sampler. With this new sampling procedure integrated subpressurized samples can be collected passively using critical orifices as an inlet mechanical flow controller. This type of flow controller acts as a point restriction for the entry of air or gas sample, and the low flow rates obtained are principally a function of the orifice size. However, the average sampling time cannot exceed a few hours because of physical limitations of the orifice size.

In the development of an overall strategy of sample collection, temporal and spatial considerations are of prime importance. It is necessary to adopt sampling strategies which recognize the inherent statistical nature of assessing air quality. Considering the environmental variability observed in ambient air levels, combined with the chronic or the carcinogenic effects associated with exposure to some chemicals, long-term average concentration provides meaningful information in terms of risk analysis.

Toxicologically, it has been suggested that sampling duration should be adapted to represent the human uptake, distribution and elimination kinetics of these harmful substances so that exposure measurements can be related to the total body burden. For many of the toxic chemicals such as volatile organic chemicals (VOCs), rates of elimination support the use of longer sampling time. Long term integrated sampling can provide a better estimate of the absorbed dose, and correlations between exposure assessment and health effects can be improved.

Statistically, it has been shown that standard deviations calculated for airborne contaminants data collected in one location, or for a class of workers, will be a function of averaging times. The distribution of mean long term integrated measurements has a smaller variance. When comparing workers mean exposure, this observation is very important in testing for compliance. It means that less data would be required to observe statistically significant differences based on legal standards or threshold limit values (TLVs) defined for the workplace. This effect of averaging time on the distribution of air quality measurements also has the same mathematical importance in data handling when environmental levels need to be established to determine global trends.

Based on a legal standpoint, definitions are also in favor of increasing the sampling duration worldwide. For environmental protection, many guidelines are defined as mean levels not to be exceeded over periods of weeks, months or a year. In a workplace, the limits established by the American Conference of Governmental Industrial Hygienists (ACGIH) correspond to normal 8-hour workday and a 40-hour workweek. Under many regulations, arguments support the application of devices which could evaluate airborne contaminants over an extended period of time.

The use of long term monitoring has been justified according to toxicological, statistical and legal criteria. For the benefit of air quality studies, it was shown that actual methodologies should be improved to overcome present drawbacks. Better sampling methods can also find application in solving engineering problems.

In process control, it is sometimes necessary to perform routine monitoring when direct on-line readings systems are not available. Indirect collection of process gases or emissions at the source is then required. For these purposes, the present methodologies have the same sampling time limitations as those found in air quality monitoring. For example, in fluctuating processes such as organic vapors biofilters and scrubbers, it is only possible to estimate the global performance of these gas treatment technologies with a repeated number of short time (hours) samples taken over a significant period (months) of operation. The overall yield is difficult to define. Long term sampling at the inlet and outlet of such technologies can improve the estimation of performance.

SUMMARY OF THE INVENTION

It is an object of this invention to provide a sampling assembly for the time integrated passive collection of a gas or ambient air.

It is a further object of this invention to provide a process of time integrated sampling of a gas.

It is a still further object of this invention to provide a sampling flow controller for time integrated flow of gas or ambient air.

In accordance with one aspect of the invention there is provided a sampling assembly for the time integrated passive collection of a gas or ambient air comprising a sample vessel having a negative atmosphere, said vessel having a gas inlet and being operatively connected to a sampling flow controller comprising an elongated capillary tube having an inlet port and an outlet port with a gas flow passage therebetween, said outlet port communicating with the vessel, said capillary tube having a length and an internal diameter selected such as to provide flow control of gas or ambient air at said gas inlet of the vessel.

In accordance with another aspect of the invention there is provided a process of time integrated sampling for the analysis of a gas comprising the steps of: introducing a gas sample at a substantially constant flow rate into an evacuated vessel along an elongated capillary tube having an inlet port and an outlet port with a flow passage therebetween, including selecting said capillary tube to be of a specified length and internal diameter to provide flow control at said outlet port and a predetermined sampling duration.

In accordance with another aspect of the invention there is provided a sampling flow controller for time integrated flow of gas or ambient air during collection comprising, in combination: an elongated capillary tube having an inlet port and an outlet port with a gas flow passage therebetween, means for communicating said outlet port with a sample vessel adapted to be held under a negative pressure, and a filter operatively connected to said inlet port for prevention of entry of particulate matter into said flow passage, said capillary tube having a length and an internal diameter selected such as to provide flow control of gas or ambient air at said outlet port.

DESCRIPTION OF PREFERRED EMBODIMENTS

This invention principally addressess problems of versatility in time integration sampling that are encountered when monitoring ambient air and gas.

The invention thus relates to an improvement in the process of time integrated sampling or monitoring for the analysis of air and gas chemistries. In the process the gas sample is introduced at a substantially constant sampling flow rate into an evacuated vessel, for example, using a critical orifice, or in a trapping media.

The improvement in said steps relates to the use of a substantially constant flow rate using the driving force of an evacuated vessel connected to a capillary tube of a specified geometry, acting as an inlet controller; providing any desired sampling duration by the selection of appropriate geometry (length and internal diameter) of the capillary tube. The selection of the geometry of the capillary tube for sampling duration and evacuated vessel size is developed from calculations using mathematical equations based on a phenomenological model.

The sampling flow controller comprises a designed inlet geometry of capillary tube which is connected to an evacuated vessel. Suitably a pressure measuring or reading device is installed between the evacuated vessel and the capillary. The sampling flow controller suitably has a filter installed at the inlet port of the capillary tube. This filter is operatively connected at the inlet port and prevents entry of particulate matter into the flow passage. The capillary sampling flow controller may also suitably include a trapping material inside a holding material connected between the capillary tube and the evacuated vessel. The sampling flow controller may conveniently have a wider internal diameter at the outlet port connected at the gas inlet of the vessel.

Samples collected with the capillary sampling flow controller can be analyzed for various air contaminants to provide mean levels over the selected integrated time.

More especially the geometry of the capillary tube is such that wherein the length and internal diameter are selected in accordance with the relationship $$L = \frac{K_6 R^4 t}{(e^{\frac{V_f}{K_5}} - 1)}$$

wherein

L is the length of the capillary in meters,

R is the internal radius of the capillary in meters, $V_f$ final sample volume in cubic meters, t is the time in seconds, and $K_5$ and $K_6$ are constants for the system in which $$K_5 = \frac{P_{atm} V_s \overline{V}}{\mathbb{R} T}$$

and $$K_6 = \frac{\pi \mathbb{R} T}{8 \mu V_s \overline{V}}$$

wherein $P_{atm}$ is atmospheric pressure (Pa)

$\overline{V}$ is the molar volume (m³/mole)

$\mathbb{R}$ is the gas constant (N.m/mol.k)

T is the temperature (°K), and $V_s$ is the volume of the vessel.

Thus the length and internal diameter of the capillary tube are selected employing mathematical equations derived from a phenomenological model.

In particular embodiments the volume of the sampling vessel will typically be from 50 ml to 50,000 ml, the capillary tube will have a length ranging from 5 cm to 500 cm and the related internal diameter of the capillary tube ranges from 0.05 mm to 0.53 mm, but small diameter tubes may be employed provided the required relationship with the length is observed.

In one particular embodiment the capillary tube is enclosed within a protective housing which may contain protective packing material which absorbs vibrations and prevents breakage of the tube during transportation or handling.

In a further particular embodiment the assembly is formed as a portable unit design to be mounted on a support, accessing a garment of a person. In such case the assembly includes mounting elements for mounting the vessel on a support which is adapted to be worn by a person, for example, a belt or shoulder harness. The vessel is then of a size and weight suitable for being carried from place to place by the person while mounted on the support. Such portable unit also includes mounting elements for mounting the inlet port of the tube adjacent the breathing zone of the person, i.e., the atmosphere adjacent the nose and mouth of the person. The inlet port might, for example, be mounted at the collar of a garment worn by the person, or from headgear worn by the person.

BRIEF DESCRIPTION OF THE DRAWINGS

Having thus generally described the nature of the invention, reference will be made to the accompanying drawings, showing by way of illustration, a preferred embodiment thereof, and in which:

FIG. 3 is a schematic view of an embodiment of the present invention used for personal sampling;

DESCRIPTION OF PREFERRED EMBODIMENTS WITH REFERENCE TO THE DRAWINGS

The sampling vessel can be made of any material able to support a high vacuum, for example, deactivated fused silica, stainless steel, aluminum, glass, Teflon (Trade Mark), metallic alloys and polymeric materials and can be of various sizes or shapes. The improvement of the invention comprises a capillary sampling flow controller (CSFC) assembled with specific dimensions in length and internal diameter of the capillary tube to deliver the appropriate flow rate during a designated period of time.

The CSFC is a sampling train basically made of two components: a pressure gauge or transducer to monitor and control the time integrative sampling process and more importantly, a capillary tube of appropriate dimensions. An inlet filter prevents the entry of particulate matter.

Figure 1:
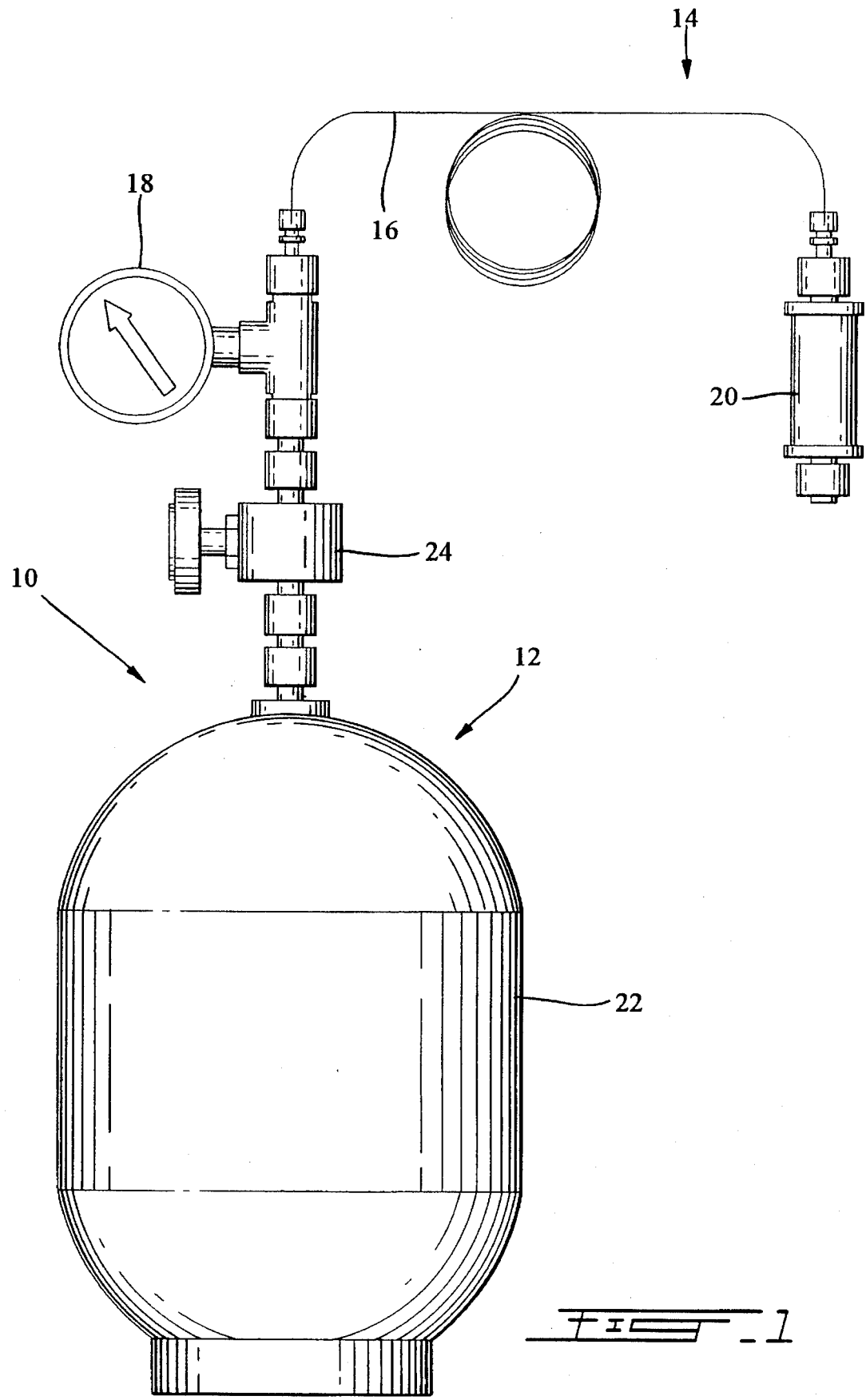
FIG. 1 is a schematic view of an embodiment of the present invention.

FIG. 1 illustrates a time integrated passive ambient air sampler assembly using the CSFC.

With reference to FIG. 1 a sampling assembly 10 includes a sampling vessel 12 and a sample flow controller 14. Sample flow controller 14 includes an elongate capillary tube 16, a pressure gauge 18 and a filter 20.

Vessel 12 has an interior reservoir 22 and a needle valve 24.

A Summa canister (available from Graseby-Anderson, Atlanta, U.S.A.) is a stainless steel vessel in which the internal surfaces have been passivated employing an electro polishing step with chemical deactivation to produce a surface which is chemically inert.

In particular, vessel 12 may be a 1 liter Summa passivated canister with a ¼ stainless steel needle valve (with Swagelok® fittings). The pressure gauge 18 is connected on-line between the sampling vessel 12 and the capillary tube 16 using appropriate leak free fittings. The capillary tube 16 such as a deactivated fused silica column, is connected between the pressure gauge 18 and the filter 20 with Swagelok® connectors and graphite-vespel ferules. In a particular embodiment filter 20 consists of a stainless steel frit of 0.5 µm porosity inside a body with ¼ or ⅛ Swagelok® connectors.

Capillary tube 16 has an inlet port at which filter 20 is connected and an outlet port communicating with a gas inlet of vessel 12. An elongate flow passage extends between the inlet port and the outlet port.

In a particular embodiment, the capillary tube 16 is a deactivated fused silica column of 0.4 mm outside diameter and pressure gauge 18 is capable of monitoring gas pressure from −30 Hg to 30 psi.

Figure 2:
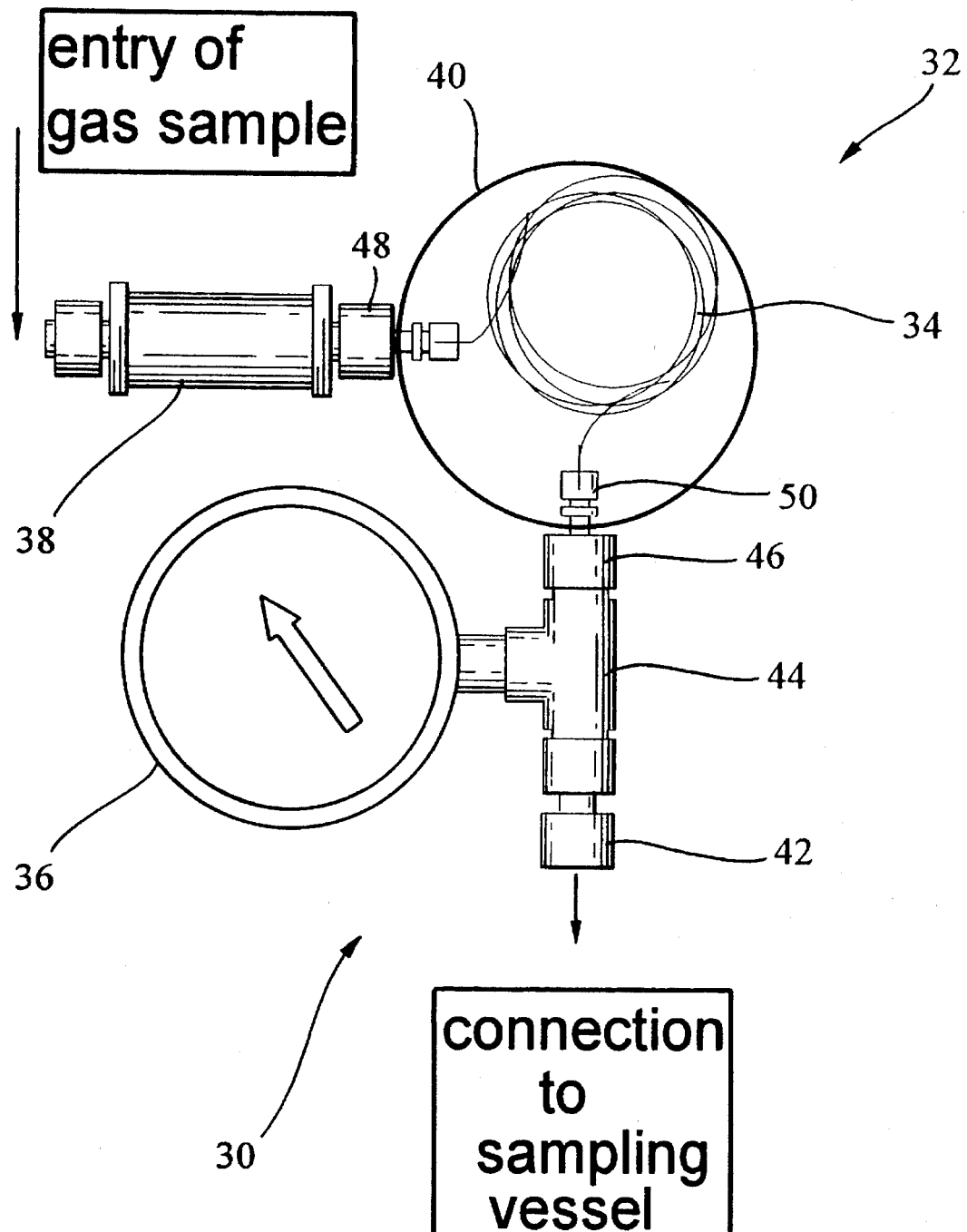
FIG. 2 is a schematic view of an embodiment of the present invention used for stationary sampling.

FIG. 2 illustrates the capillary sampling flow controller as a stand-alone unit 30. Unit 30 comprises a sample flow controller 32 with a connection element 42 for connection to a sampling vessel.

Sample flow controller 32 includes an elongate capillary tube 34, a pressure gauge 36 and a filter 38.

Elongate capillary tube 34 is housed in a protecting shield 40.

A fitting 44 interconnects pressure gauge 36, connection element 42 and fitting 46 which connects to a fitting 50 at the outlet port of tube 34. Fitting 48 connects filter 38 at the inlet port of tube 34.

In one embodiment fitting 48 is a 0.25" Swagelok; fitting 46 is a 0.0625 to 0.25" Swagelok reducer; fitting 44 is 0.25–0.25 Swagelok union; fitting 50 is a 0.125"–0.4 mm graphite-vespel ferrule; filter 38 is as for filter 20 in FIG. 1; tube 34 is a deactivated fused silica tube; shield 40 is a cylindrical enclosure 50 mm outside diameter; and pressure gauge 36 is a bourdon tube device 0.25" NPT -30" Hg to 30 psi. Here, the appropriate geometry of capillary tube 34 is enclosed in the protecting shield 40. This shield 40 is attached on the Swagelok® reducer fittings which join the capillary tube 34 between the filter 38 and the appropriate connection to the pressure gauge 36 or to the evacuated vessel. The protecting shield 40 can be machined from stainless steel and welded to the fittings. This protective shield or casing 40 can then be filled with any packing materials that will absorb vibrations and prevent the capillary tube from breaking during transportation or handling. The capillary tube 34 can also be incorporated into a plastic material using epoxy, polyacrylic or other polymeric resins. This latter type of protecting shield is cast using resin transfer molding directly on the capillary tube 34 and fittings which are installed in an appropriate mold.

FIG. 3 shows a schematic configuration of a portable personal sampler for gaseous contaminant using the CSFC.

With further reference to FIG. 3 a portable sampling device 60 includes a sampling vessel 62 and a sample flow controller 64.

Sample flow controller 64 includes an elongate capillary tube 66, and a sampling line 67. A filter 68 is connected to an inlet port of sampling line 67, and sampling line 67 has an outlet port connected to an inlet port of tube 66; tube 66 is housed in a protective housing 70.

Vessel 62 has mounting clips 72 (schematically shown) to mount vessel 62 on a belt worn by a person and filter 68 has mounting clips 74 (schematically shown) to mount filter 68 on the collar of a garment worn by the person.

Basically, this sampling device 60 is similar to those Shown in FIGS. 1 and 2. However, the evacuated vessel 62 is small enough (less than 200 ml) to be carried on a belt worn by a person. This sampling train does not include a pressure gauge because of size limitations but may include a pressure indicator/sensor. The inlet filter 68 is attached to the person's collar to collect breathing zone air samples. The sampling line 67 preferably made of Teflon (Trade Mark) tubing (OD ¹⁄₁₆", ID 0.3 mm) connects the sampler maintained at the belt to the filter 68 attached near the breathing zone. The CSFC is designed with the appropriate length of tube 66, for example, a deactivated fused silica tubing having an internal diameter less than 0.3 mm. Tube 66 is enclosed inside protecting housing 70 or shield 70. Capillary tubes of 0.05 mm, 0.10 mm and 0.18 mm internal diameter are commercially available and offer the selection of any sampling time. Multi capillary tubing is also available and may be used alternatively. The design of CSFC applied either for personal monitoring or stationary sampling is always based on the same principles. The configuration of samplers can be adapted, to meet specific requirements.

Once assembled, the passive sampling unit made with the CFSC connected to an evacuated sampling vessel has to be tested for leaks. For that purpose, a cap is installed on the entry of air in the system, i.e. the filter. By opening the valve, the pressure gauge should read the low pressure inside the vessel and if the system is airtight, this vacuum will be maintained. An overnight check using this procedure is recommended. More sophisticated procedures can also be implemented using sensitive gas detectors when the sampling train is pressurized in close-circuit. This can provide a faster verification and certification of the sampling system.

With this invention, the pressure gradient between ambient air or process gases and the evacuated sampling vessel, acts as the driving force. Because motion can be controlled with the appropriate geometry of inlet restrictive capillary column, the system delivers a precise air sampling flow rate and hence, time integrated air samples can be collected. Sampling becomes completely passive, independent of any power requirement. The monitoring of air quality or process gases using this invention becomes fairly simple. The only operation steps consist in opening the valve (manually or automatically) at the beginning of the sampling period and closing it after the selected duration. To obtain a constant flow rate over the integrated sampling period, desirably the vessel should only be filled to approximately 40% to 60–65% of its total volume. If this is exceeded, the flow rate starts to decrease, the driving force being insufficient. Compared to systems employing the critical orifice inlet restriction, the capillary sampling flow controller can cover any time periods desired, and it can provide a much lower flow rate. Instead of being a point restriction, it offers a fully characterized line restriction.

RESULTS

The volumetric flow rate between the inlets of a pipe is related to the pressure gradient, the viscosity of the fluid and the pipe dimensions when a laminar flow of a Newtonian fluid is established. Also, many gas matrices including air normally behave as a perfect gas, and relationships between pressure, volume, molar concentration and temperature are well established in these situations. In order to characterize and predict the passive sampling process obtained with the CSFC prototype, a phenomenological model was developed after stating simplifying assumptions. It was developed from two different known equations that were modified and adapted to correlate the long term sampling process that is observed with the CSFC. The first relationship is based on fluid mechanics: the Hagen-Poiseuille equation. The other relationship is based on a fundamental gas kinetic equation: the ideal gas law. To present the mathematical model developed to design a CSFC, a description of how these two relationships were used and which hypothesis were stated is given here:

The Hagen-Poiseuille relationship applies to a laminar flow of fluids in circular tubes. The development starts with a momentum balance using a volume element: a cylindrical shell. The momentum balance where forces from friction+compressibility+pressure and gravity =0 was stated as:

$$(2\pi r L \tau_{rz})|_r - (2\pi r L \tau_{rz})|_{r+\Delta r} + (2\pi \Delta r v_z)(\rho v_z)|_{z=0} - (2\pi \Delta r v_z)(\rho v_z)|_{z=L} + 2\pi \Delta r (P_o - P_L) = 0 \quad (1)$$

The fluid can be assumed to be incompressible (i.e. the velocity is constant over the length of the tube), only the friction and the pressure component forces are considered. Then, taking the limit as $\Delta r$ goes to zero, this gives:

$$\lim_{\Delta r \to 0} = \left\{ \frac{(r\tau_{rz})|_{r+\Delta r} - (r\tau_{rz})|_r}{\Delta r} \right\} = \left\{ \frac{P_0 - P_L}{L} \right\}_r \quad (2)$$

This expression can be written as:

$$\frac{d}{dr}(r\tau_{rz}) = \left\{ \frac{P_0 - P_L}{L} \right\}_r \quad (3)$$

In order to integrate the equation, the appropriate boundary conditions (at r=0, the shear stress is not to be infinite) were stated to obtain this solution:

$$\tau_{rz} = \left\{ \frac{P_0 - P_L}{2L} \right\}_r \quad (4)$$

Then, use the Newton law of viscosity for this situation:

$$\tau_{rz} = -\mu \frac{dv_z}{dr} \quad (5)$$

Combining the equation (4) and the Newton law, this gives the following differential equation for the velocity:

$$\frac{dv_z}{dr} = -\left\{ \frac{P_0 - P_L}{2\mu L} \right\}_r \quad (6)$$

The integration, using another boundary condition where the velocity is null at the fluid-solid interface (i.e. $v_z = 0$ at r=R) will result in the velocity distribution which gives:

$$v_z = \frac{(P_0 - P_L)}{4\mu L} r^2 \left[ 1 - \left(\frac{r}{R}\right)^2 \right] \quad (7)$$

This expression indicates that the velocity distribution for laminar flow of incompressible fluids is parabolic. From this expression, we can obtain another equation such as the average velocity:

$$<v_z> = \frac{\int_0^{2\pi} \int_0^R v_z r\, dr\, d\theta}{\int_0^{2\pi} \int_0^R r\, dr\, d\theta} = \frac{(P_0 - P_L)R^2}{8\mu L} \quad (8)$$

From the average velocity equation, we can obtain the volumetric flow rate which is the product of the cross sectional area of the cylinder ($\pi R^2$) by the average velocity as defined in equation (8). This is a rather famous result which was called the Hagen-Poiseuille law in honor of the two scientists who derived the formulation around 1840:

$$Q = \frac{\pi(P_0 - P_L)R^4}{8\mu L} \quad (9)$$

Among assumptions that relate to this equation, first the tube should be long enough, so that end effects can be neglected. This relationship also applies only to laminar flow (i.e. Reynold number less than 2100) and Newtonian fluids. The fluid should behave like a continuum—this assumption is theoretically not valid for very dilute gases or very narrow capillary tubes, in which the molecular mean free path can be higher than the tube diameter and where we observe a slip flow or free molecular flow regimes. Finally, since the Hagen-Poiseuille equation is valid under steady-state, the flow should be time independent.

This mathematical development {from equation (1) to equation (9)} was developed long ago and was described elsewhere. In order to characterize the behavior of a CSFC, we have made the assumption that in a pseudo steady-state system, the volumetric flow rate and the internal sampling vessel pressure should both be a function of time: the sampling time. Also, in this process, $P_0$ is equal to atmospheric pressure ($P_{atm}$) and internal pressure of the vessel is variable {P(t)}. This gives the following expression:

$$Q(t) = \frac{\pi(P_{atm} - P(t))R^4}{8\mu L} \quad (10)$$

The assumption is made that the air viscosity between the vacuum and ambient pressure remains constant. Remember that Hagen and Poiseuille also had to assume that the fluid density remains unchanged, which is certainly not the case considering the pressure differences over the CSFC operating range. Equation (10) is one of the original mathematical expressions used to develop the phenomenological model applied to the design of a CSFC. However, to obtain the set of equations, a second relationship has to be postulated.

In order to characterize the behavior of a CSFC as to the relation between the flow rate and the internal pressure, we have started with this fundamental relation based on kinetic theory of gases called the ideal gas law relationship:

$$PV = n\mathbb{R}T \quad (11)$$

This equation is restated, considering the variation of two variables which are a function of sampling time (the internal sampling vessel pressure and the molar content):

$$P(t) = \frac{n(t)\mathbb{R}T}{V_S} \quad (12)$$

Now, as in the behavior of a critical orifice when used on evacuated vessels, the volumetric flow rate remains constant during the time it required to fill more than half of the sampler's volume. Therefore in part of the process the sampled volume is expressed as:

$$V(t) = \int_0^t Q(t)\, dt \quad (13)$$

and if the flow rate is constant as we find experimentally:

$$V(t) = Q(t)t \quad (14)$$

We finally relate the sampled volume with the molar content using the molar volume at standard temperature and pressure. We write:

$$n(t) = \frac{V(t)}{\overline{V}} = \frac{Q(t)t}{\overline{V}} \quad (15)$$

Taking this expression and replacing in equation (12), we obtain:

$$P(t) = \frac{\mathbb{R}TQ(t)t}{V_S \overline{V}} \quad (16)$$

This last relationship is the second equation used to derive the phenomenological model developed to predict the geometry of a capillary column for the design of a novel flow controller: the capillary sampling flow controller.

The model was derived by resolving equation (10) and equation (16) in which one of the two unknown variables {P(t), Q(t)} can be removed to obtain a single equation. By the elimination of the internal pressure time function {P(t)}, we have obtained an expression of the volumetric flow rate {Q(t)} which is a function of the sampling time (t). We have expressed this equation with two constants ($K_1$, $K_2$) which have no physical meaning. This relationship is:

$$Q(t) = \frac{K_1}{1 + K_2 t} \quad (17)$$

where:

$$K_1 = \frac{\pi P_{atm} R^4}{8\mu L} \quad (18)$$

$$K_2 = \frac{\pi \mathbb{R} T R^4}{8\mu L V_s \overline{V}} \quad (19)$$

Again, using the same two equations we have obtained the pressure variable {P(t)} as a function of the sampling time by here, removing the flow rate variable. Again, two constants were defined ($K_3$, $K_4$) and this expression is:

$$P(t) = \frac{K_3 P_{atm} t}{K_4 - K_3 t} \quad (20)$$

where:

$$K_3 = \frac{\pi \mathbb{R} T R^4}{\overline{V}} \quad (21)$$

$$K_4 = 8\mu V_s L \quad (22)$$

Finally, to compute the sampled volume variations versus the sampling time, we have integrated the flow rate expression {equation (17),(18),(19)}:

$$V(t) = \int_0^t Q(t)dt = \int_0^t \frac{K_1}{1+K_2 t} \quad (23)$$

Resolving this equation, we have defined two other arbitrary constants ($K_5$, $K_6$) and obtained a solution for the sampled volume as a function of time integration {V(t)}:

$$V(t) = K_5 \ln\left(1 + \frac{K_6 R^4}{L} t\right) \quad (24)$$

where:

$$K_5 = \frac{P_{atm} V_s \overline{V}}{\mathbb{R} T} \quad (25)$$

$$K_6 = \frac{\pi \mathbb{R} T}{8\mu V_s \overline{V}} \quad (26)$$

Finally, we have defined a value of V(t) equal to the final sampled volume ($V_f$) which should be between 0.5 and 0.7 of the sampler volume ($V_s$). Then, we obtained an expression of inlet restriction length of capillary (L) as a function of the sampling time (t). This relationship can be used to design a CSFC, considering a specified internal diameter of capillary column. This final relationship is:

$$L = \frac{K_6 R^4 t}{(e^{\frac{V_f}{K_5}} - 1)} \quad (27)$$

Notations:
L Length of inlet restrictive deactivated fused silica capillary column (m)
n Number of moles (mole)
n(t) Molar content time function (mole)
$P_0$ Inlet pressure inside capillary (Pa)
$P_L$ Outlet pressure inside capillary (Pa)
$P_{atm}$ Atmospheric pressure (Pa)
P(t) Sampling pressure time function (Pa)
Q(t) Volumetric sampling flow rate time function (m³/s)
r Radial distance in cylindrical coordinate (m)
R Internal radius of restrictive deactivated fused silica capillary column (m)
  Gas constant (N·m/mole·K)
t Integrated sampling time (sec)
T Temperature (°K)
V Molar volume (m³/mole)
V(t) Sampled volume time function (m³)
$V_f$ Final sampled volume (m³)
$V_s$ Canister sampler volume (m³)
$v_s$ Velocity of fluid in longitudinal direction (m/s)
z Longitudinal distance in cylindrical coordinate (m)
Symbols:
θ Angle in cylindrical coordinate (radian)
$\tau_{rz}$ Shear stress (N/m²)
ρ Fluid density (kg/m³)
π 3.14159 . . .
μ Viscosity of air (poise)

This model was developed to estimate the geometry of the capillary in order to obtain a desired sampling time, whatever the sampler's volume. It does not characterize the velocity profile along the capillary.

Figure 4:
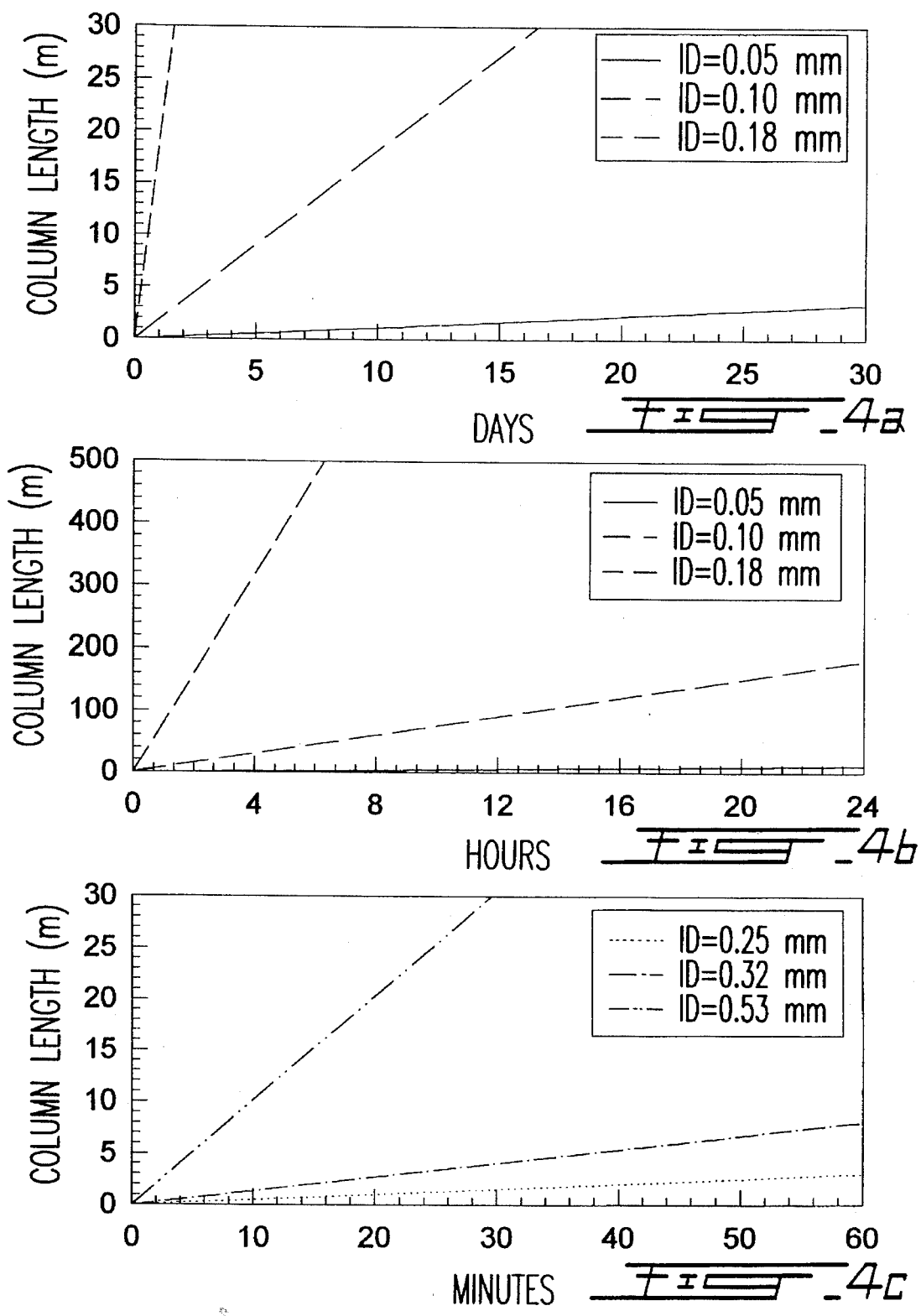
FIGS. 4a, 4b and 4c are graphs showing predicted design parameters of capillary flow based on present embodiment.

From these considerations, the model predicts the sampling behavior for any size of evacuated sampling vessels such as Summa canisters, and estimate CSFC characteristics (internal diameter and length of capillary column) for a desired sampling period. FIGS. 4a, 4b and 4c shows predicted design parameters of the capillary flow controller based on this model, when a 1 liter sampling vessel is used to collect 500 ml of sampled air (half-volume subpressurized samples). It can be seen that capillary internal diameter drastically affects the sampling time. Internal diameter greater than 0.25 mm would require very long length of capillary to restrict the flow and obtain sampling duration exceeding a few hours. However, the smallest internal diameter simulated (i.e 0.05 mm) offers wide passive integrated sampling times without using long lengths of capillary (i.e. approximately 4.5 meters of column for a sample duration of 30 days with a one liter vessel). These simulations can easily be performed with other sizes of sampling vessel and other internal diameters of capillary lines using the original model. Also the atmospheric pressure used in the model can be replaced by other inlet pressure when applied inside special locations (positive or negative pressure chambers) or for process monitoring.

Figure 5:
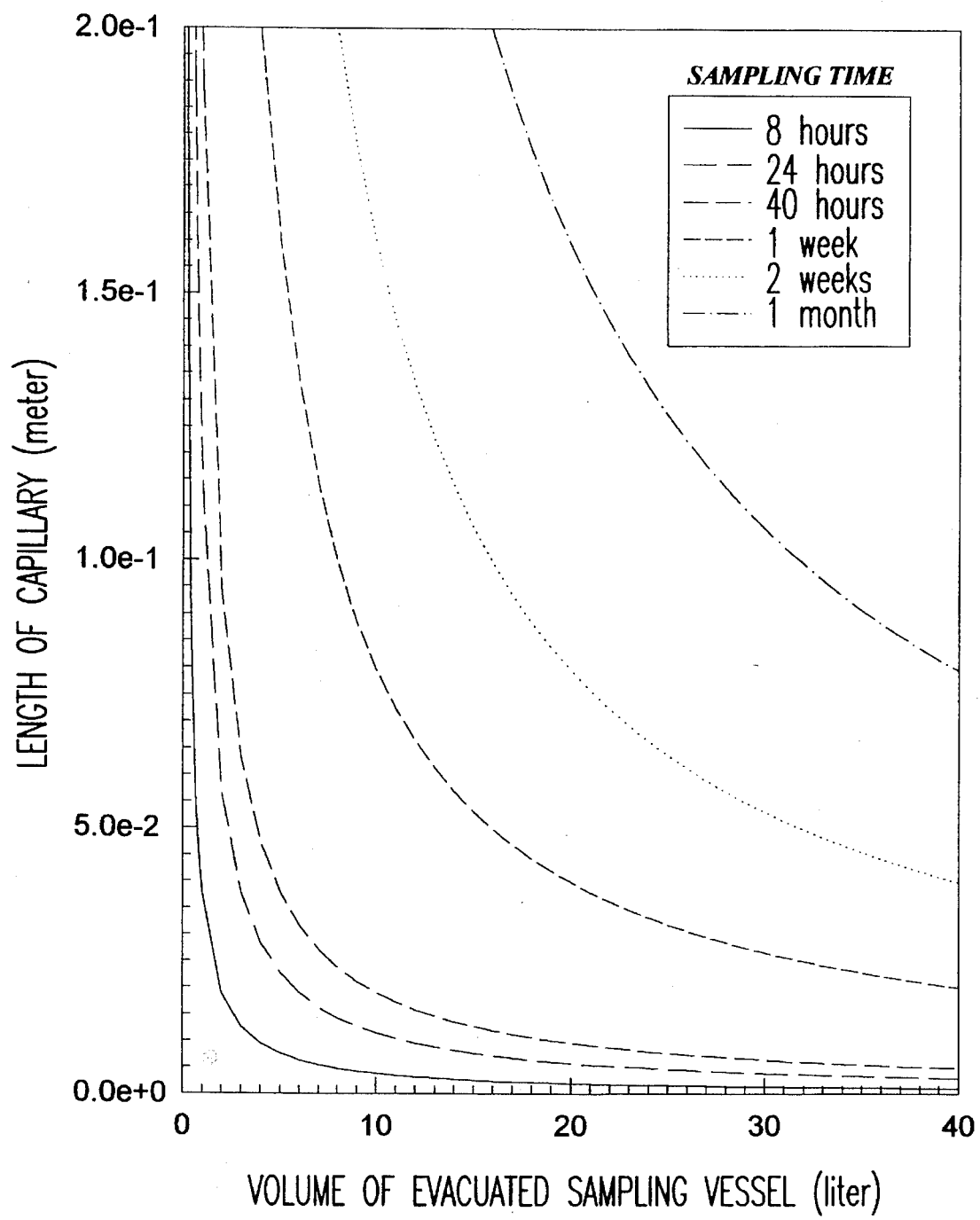
FIG. 5 is a graph showing a prediction of capillary length for long term sampling.

An investigation was made of the impact of sampler size (internal volume of vessel) on the design of CSFC using a 0.05 mm ID capillary. Simulations were performed to evaluate the lengths of capillary to achieve different sampling times with different sampling vessel sizes. For samplers ranging from 100 ml to 40 liters, FIG. 5 illustrates the predicted length of capillary (from 0 to 200 cm) that a CSFC would need to integrate sampling time from 8 hours to one month. As the size of the sampler increases, the length of capillary rapidly decreases up to a point where variations in length can have an important effect on sampling time. In fact, these data show that short capillary tube (less than 5 cm) used to obtain specific sampling times is less accurate and this observation was also verified experimentally. This means that when bigger vessels (>5 liters) or short sampling time (<40 hours) are required, a capillary tube with larger internal diameter should be used in the design.

The theoretical effect of temperature affecting viscosity and molar volume was also simulated for a specific CSFC unit. The Sutherland's relationship was used to compute values of viscosity at different temperature. The predictive results showed the minor impact of ambient temperature on the overall sampling time and on the functioning of the invention. The shape and material of both vessel and capillary have no impact on flow control process. The major controlling factor is the total length of a specified internal diameter of capillary column or capillary tubing.

Figure 6:
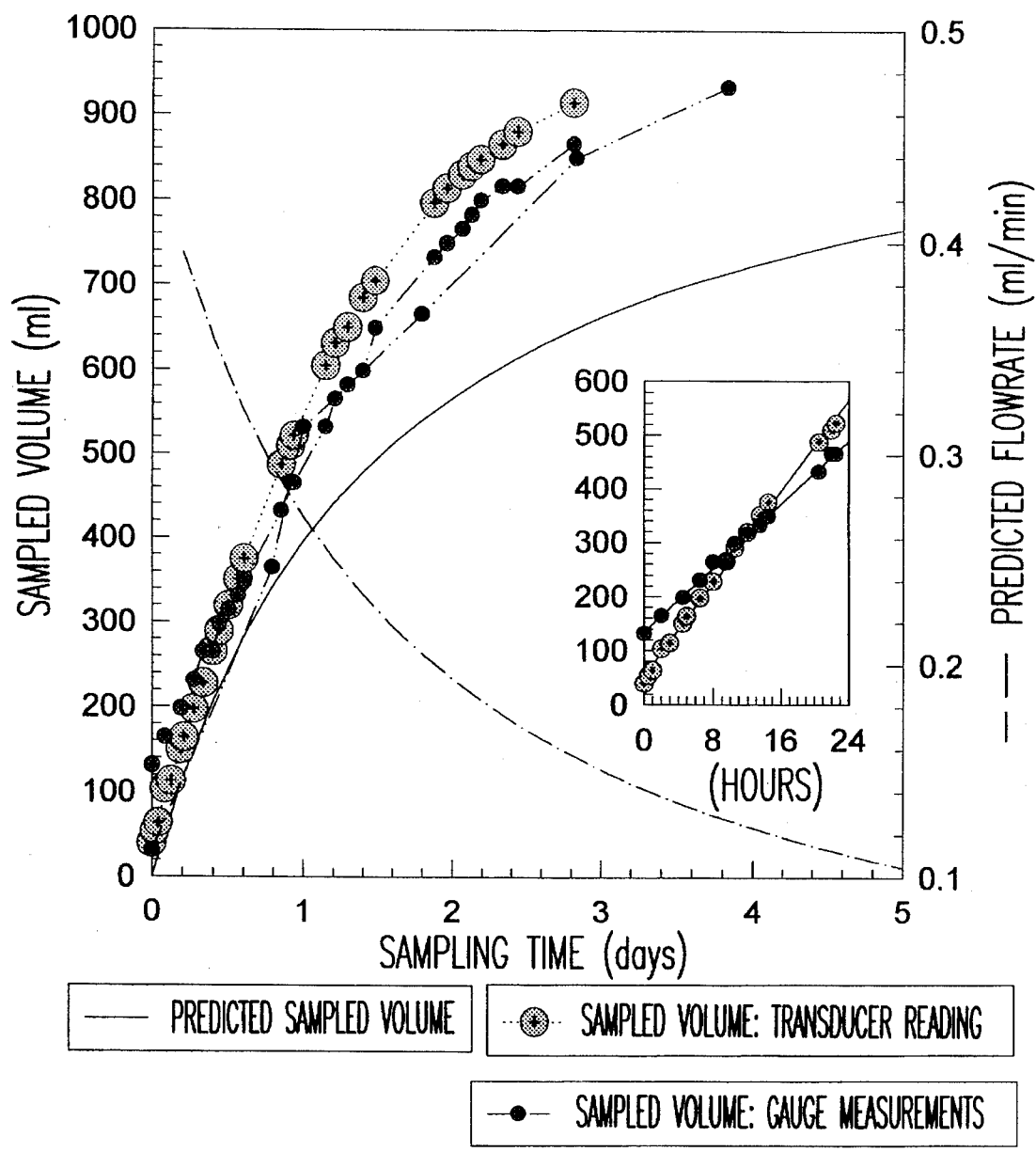
FIG. 6 is a graph showing the results from experiments using a selected length of capillary.

Many studies were performed to evaluate the performance of this invention. Investigation with different sizes of gas collection vessels using CSFC prototypes assembled with different lengths of fused silica capillary columns of 0.05 mm internal diameter were conducted to characterize the long-term sampling behavior. Generally, the mathematical model was shown to give good approximations for the appropriate geometry of capillaries. Results from experiments using predicted length (0.115 meter) of the capillary tube and internal diameter of 0.25 cm are presented in FIG. 6. for a temperature of 25° C. and an inlet pressure of 1 atm. The sampled volume (data points) are based on pressure readings taken during time intervals. Two different readings are reported: one obtained from an electronic pressure transducer, others taken from a simple mechanical pressure gauge (Bourdon type). These data along with predicted pressure function were transformed into sampled volume using perfect gas law relations (FIG. 6, left axis). The pressure behavior which served to derive the predicted sampled volume was computed from equations (20),(21) and (22).

Figure 7:
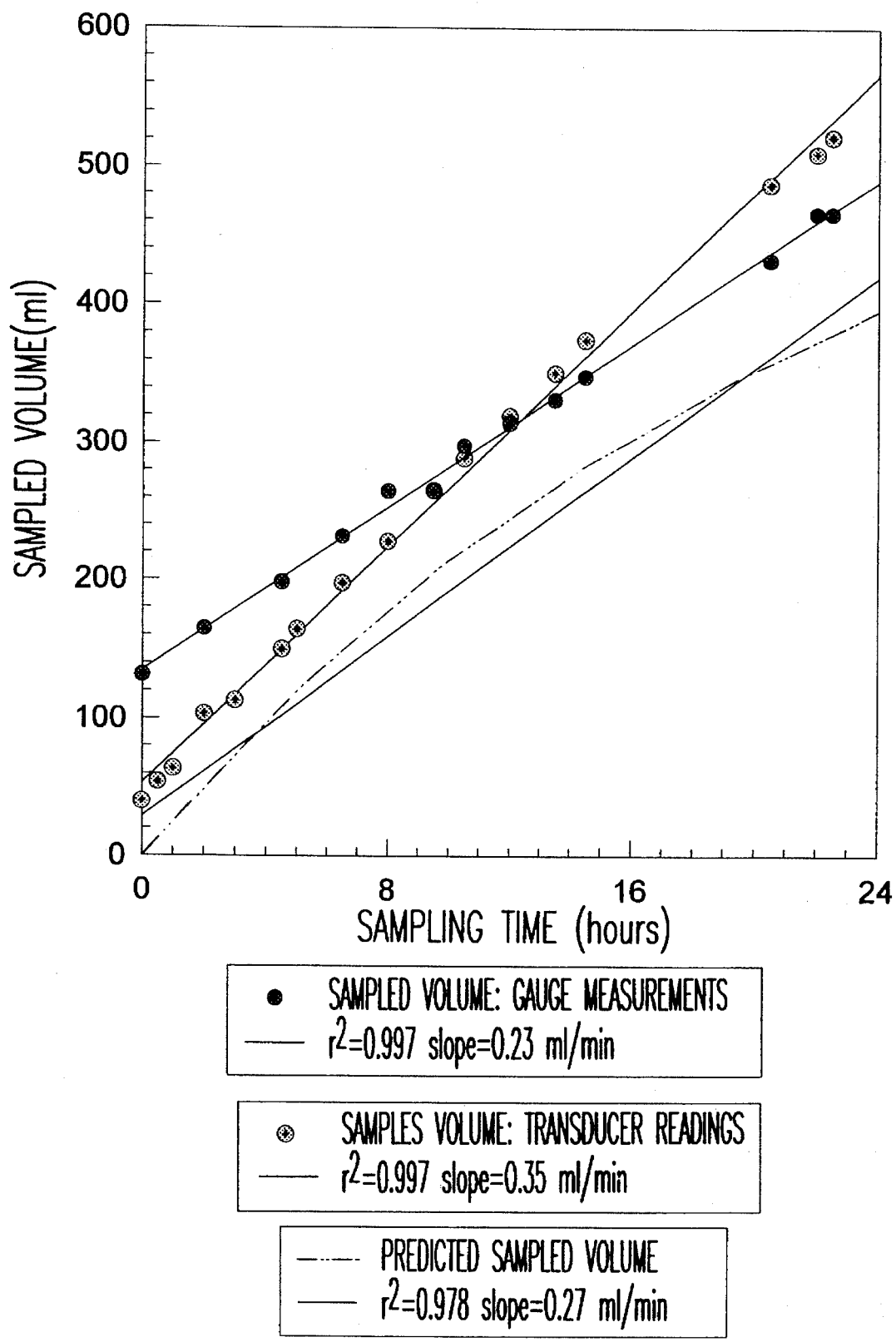
FIG. 7 is a graph showing a linear approximation over a 24-hour period of sampling by the present invention.

Flow rate predictions from model simulations are also reported on this graph (FIG. 6, right axis) and they were calculated from equations (17), (18) and (19). The CSFC was able to extend the duration of sampling 500 ml of ambient air for 24 hours. During this period, a linear relationship between sampled volume and time can be observed. The model prediction could very well estimate the time integration capability of this prototype although it does not reproduce entirely the experimental findings. In order to approximate the sampling flow rate during the first 24 hours, the data obtained was linearized from the prototypes and from the predictive model. These results are found in FIG. 7, for a 0.115 m length, 0.05 mm diameter and 1 liter volume. FIG. 7 shows that the CSFC can easily deliver a constant sampling flow rate (between 0.23 ml/min to 0.35 ml/min) to collect an integrated passive sample of ambient air over its operating range. In fact, the model predicts a saturation process and hence, a less constant flow rate than what is observed experimentally. The regression coefficients ($r^2$) was higher in experiments (0.997) compared with those obtained from the theoretical relationship (0.978 for a slope of 0.27 ml/min). These experimental results demonstrate the validity of time integration properties gained with the CSFC. The small flow rate variation observed between prototypes can be explained by the differences in initial vacuum between samplers, or by calibration errors in pressure measuring devices. This has negligible effects on the linearity of sampled volume during the passive process.

Figure 8:
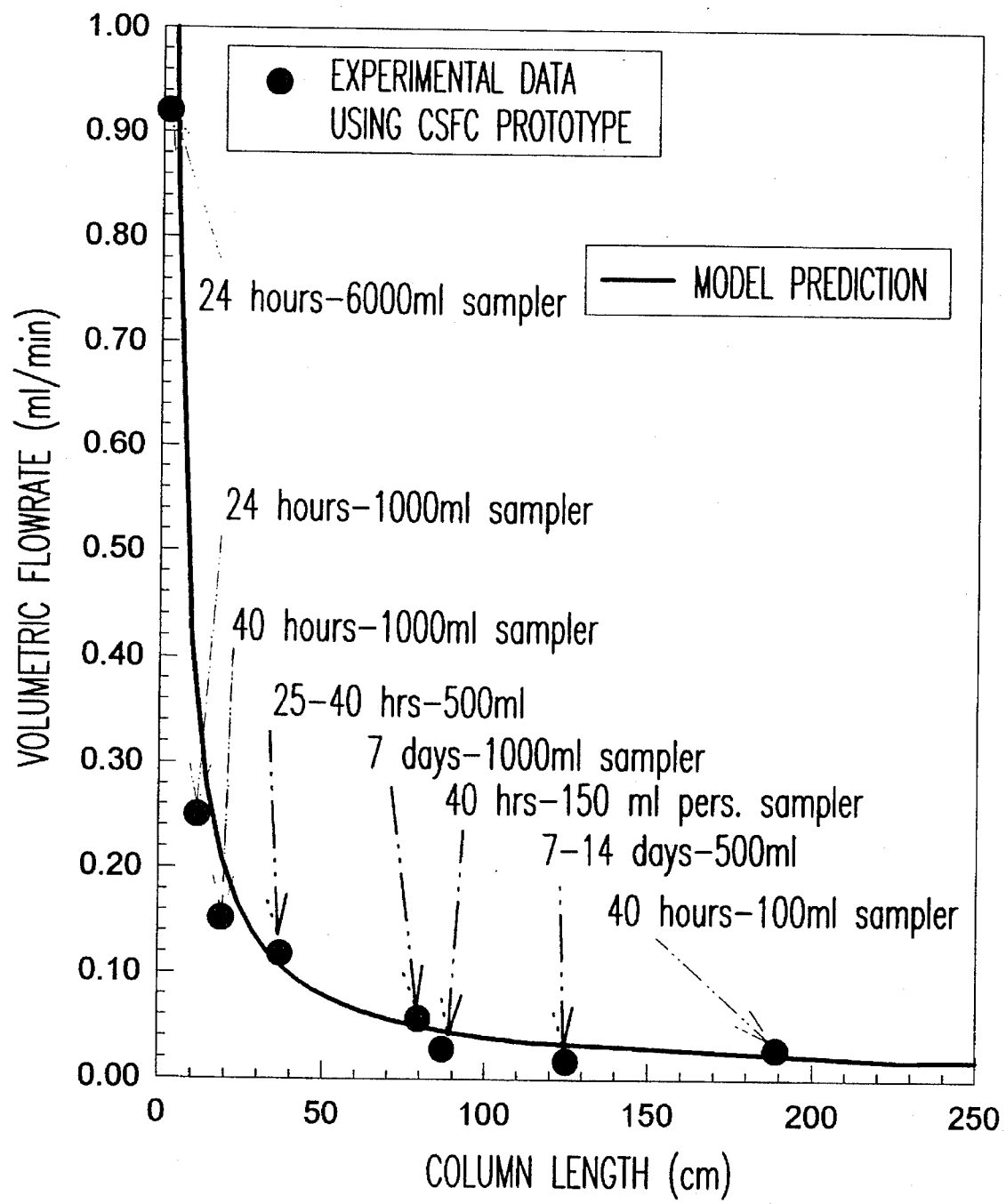
FIG. 8 is a graph showing the relationship between the length of capillary and the passive sampling flow rates delivered by the present invention.
Figure 9:
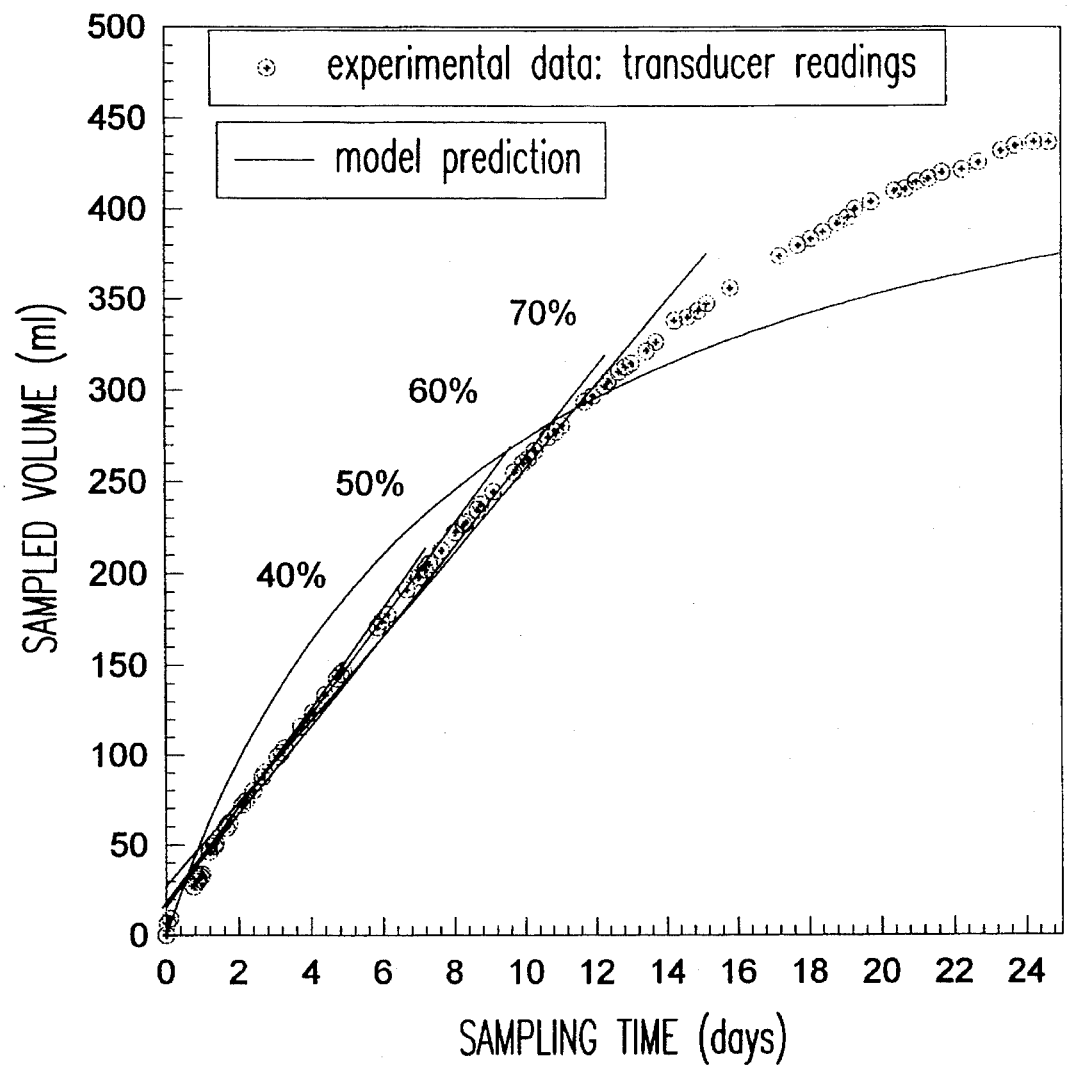
FIG. 9 is a graph showing experimental results where linear regressions were made to study the influence of final sampled volume on the flow rate given by the present invention.

Similar experiments were repeated to verify other integrated sampling times using many sizes of sampling vessel. These studies were accomplished to demonstrate the versatility of the CSFC and validate simulation results. Until now, the same effects have been observed: a constant flow rate can be achieved, until the internal pressure inside the vessel reaches a value between 0.5 to 0.65 atm. Using different lengths of deactivated fused silica capillary having a 0.05 mm internal diameter, the performance of this new mechanical flow controller was tested to estimate volumetric flow rates. Experiments were conducted using CSFC prototypes connected with vessels having sizes of 0.1; 0.5; 1 and 6 liters. A rectangular vessel machined from stainless steel having 150 ml volume (as schematically illustrated in FIG. 3) which can be applied for personal monitoring was also tested. From the data obtained, the experimental flow rate was calculated using linear regressions. These results are presented in FIG. 8 for a capillary tube of 0.05 mm diameter. The volumetric flow rates delivered by the CSFC given the capillary lengths are compared with the predicted relationship obtained from the model. The data points derived from individual experiments using various configurations of gas samplers follow closely the curve calculated from the model using theoretical considerations. In order to investigate in more detail the effect of the final sampled volume on the consistency of the volumetric flow rate offered by the CSFC, linear regression were made whether 40%, 50%, 60% or 70% of the sampler size was collected. These results are illustrated in FIG. 9. This experiment was made in a laboratory using a 500 ml Summa canister, a tube length of 1.25 m and diameter of 0.05 mm, a temperature of 25° C. and inlet pressure of 1 atm. and data were taken over more than three weeks. FIG. 9 shows that when more than 60% to 65% of the vessel is filled with the gas sample, the pressure gradient is not sufficient to deliver a precise passive constant sampling flow rate. Otherwise, when such low flow rates are achieved, the operating range of this mechanical controller can provide very broad integrated sampling times, in this case ranging from 7 to almost 14 days. Table 1 summarize the results calculated from this analysis. Regression coefficients which are related to the precision of the sampling rate were over 99% during a large interval of time. Volumetric flow rate was maintained at 0.018±0.001 ml/min over a long integrated sampling time. This particular configuration of passive sampler which required a CSFC designed with 1.25 meters of capillary having an internal diameter of 0.05 mm was developed to be applied inside the Russian orbital station Mir.

TABLE 1

| final sampled volume | | integrated sampling duration | volumetric sampling flow rate | correlation coefficient ($r^2$) |
|---|---|---|---|---|
| (ml) | (%) | (day) | (ml/min) | % |
| 200 | 40 | 7 | 0.019 | 99.6 |
| 250 | 50 | 10 | 0.018 | 99.6 |
| 300 | 60 | 12 | 0.017 | 99.3 |
| 350 | 70 | 15 | 0.016 | 98.9 |

The behavior or other internal diameters of capillary inlet restriction were also investigated. The predicted length of capillary (ID 0.10 mm) to obtain a 24 hour integrated sampling time using a 6 liter evacuated vessel was found to be within 10% error. The validity of using two different ID of capillary linked together with a vacuum connector was tested. The purpose was to verify if a sample could be collected meters away from the vessel, where access is restricted and/or hazardous. A 5 meter long capillary with a wider internal diameter (ID 0.25 mm) connected to the appropriate length of restrictive capillary (ID 0.05 mm) was used. The wider capillary did not influence the overall time integration controlled by the smaller diameter capillary. This important result demonstrates that the CSFC can be used to collect samples some distance away from the samplers.

Experimental results supported by extensive model simulations proved that the CSFC can effectively be used for time integrated passive collection of gas and ambient air with evacuated sampling vessels. The demonstration was principally applied to long-term sampling which is still impossible using present methodologies. The CSFC can also be used for short sampling periods. The relationships between the geometry of capillary (total length and internal diameter) with relevant factors including sampling time and sampler size were established. This most valuable set of equations provides the basis to estimate CSFC geometry according to selected sampling time and sampler size. Simple experimentation can confirm the estimate or provide the information required to adjust precisely the length of capillary needed to meet the passive time integrated sampling period desired.

The capacity of the CSFC to average sampling time is one of its major attributes. Extended sampling periods which can be obtained from the CSFC can contribute to a better and faster evaluation of mean exposure. For example, five daily samples are required at present to assess worker exposure to workplace contaminants over a period of one week. With an appropriate CSFC, a unique sample taken separately for eight hours during each working day would estimate mean exposure adequately. The sampler would only have to be opened and closed at the beginning and end of a work shift. It can also be used to sample sporadic contaminant release episode to determine the nature of airborne chemicals.

Special procedures are required to analyze components of a gas matrix collected as subpressurized samples inside sampling vessels. For volatile organic chemicals (VOC) such as aromatic (benzene, toluene, xylenes, etc), halogenated (vinyl chloride, chloroform, dichloromethane, etc) and other classes of toxic chemicals, a gas chromatograph coupled with a benchtop mass spectrometer (GC/MS) may play an important role in the laboratory. These analytical instruments provide a means to quantify subppb(v) levels of target contaminants using predominant ions of full scan mass spectra, combined with the retention times of signals acquired from the chromatograms. In most GC/MS techniques developed for the analysis of VOC in ambient air, an injection unit is used to preconcentrate the VOC prior to the analysis. For this purpose, cryogenic or sorbent trapping can be used and normally, special water management procedures such as sorbent dry purging need to be implemented to maximize the sensitivity of the mass spectrometer detector.

Figure 10:
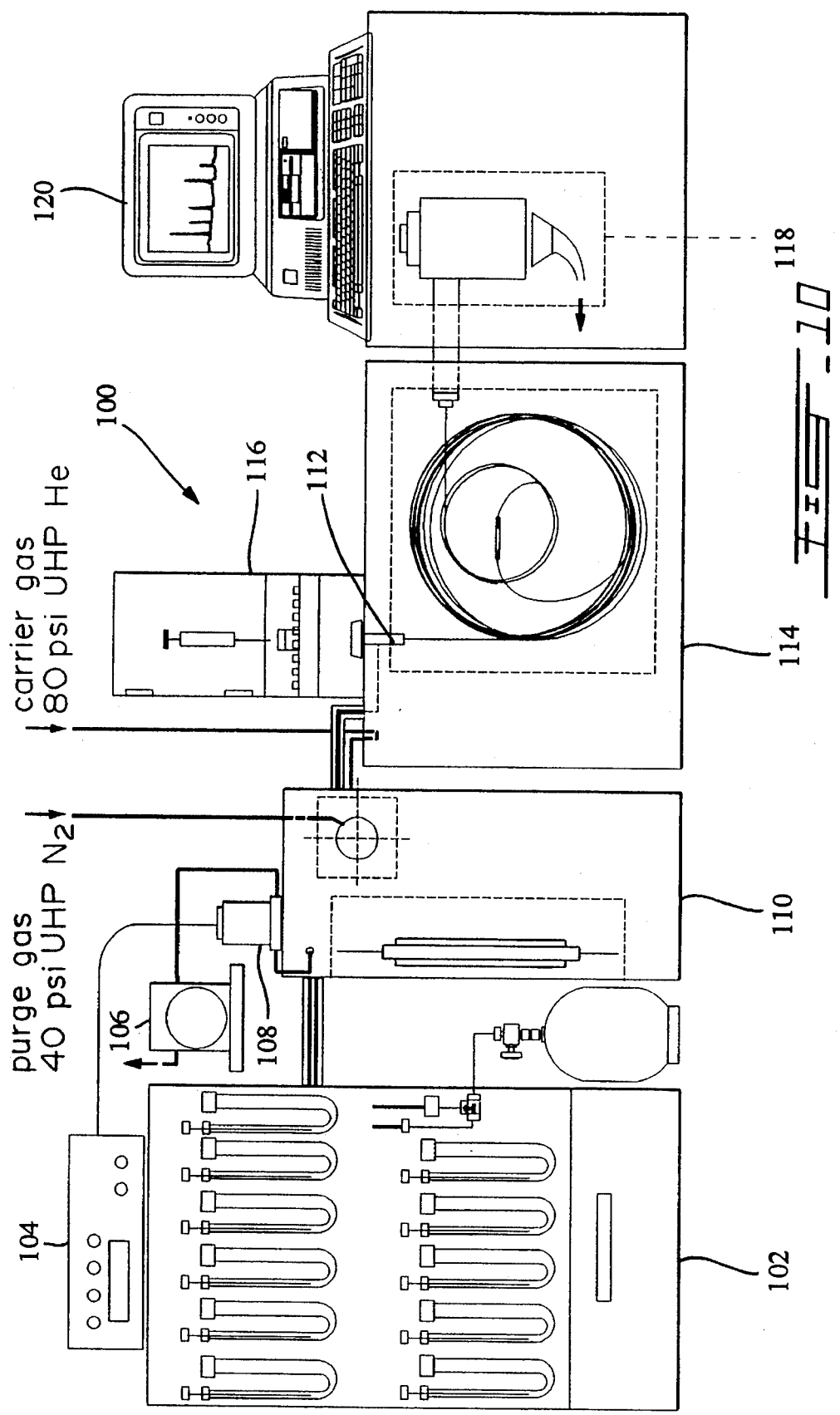
FIG. 10 is a schematic view of a laboratory system used to analyze gas samples collected using the present invention.

FIG. 10 illustrates the analytical system that was used to characterize the levels of VOC in the validation and field studies where gas samples were collected with the controller.

With further reference to FIG. 10, an analytical assembly 100 includes a purge and trap autosampler 103, a flow measurement read-out box 104, a diaphragm vacuum pump 106, a mass flow controller 108, a purge and trap describing unit 110, a direct split interface 112, a gas chromatograph 114, an autosampler syringe injector 116, a mass spectrometer detector 118 and a computer control station 120.

Thus a purge and trap injection device was modified. One purge vessel was bypassed and replaced by a three-way valve using appropriate tubing and connectors to allow the injection of gas samples from vessels. The mass flow controller 108 was connected between the vent port of this unit and the vacuum pump 106 that is used to pull out the sample into the sorbent trap. Analytes are trapped at constant flow rate during a known time interval, dry purged, thermally desorbed and transferred into the gas chromatograph 114/mass spectrometer 118. In this system, a direct split interface 112 is used to connect the purge and trap injector with the gas chromatograph 114. The vessel can be connected directly to the system, and gas samples are handled and analyzed for VOC. When the sample does not need analytical enrichment, a more simple injection device and analytical detectors can be used. For the analysis of gases such as carbon dioxide ($CO_2$), carbon monoxide (CO), nitrogen ($N_2$), oxygen ($O_2$) and methane ($CH_4$), sample aliquots can be taken from a gas tight syringe and injected directly to an on-column port of the gas chromatograph column 114. Simpler detectors based on electrical conductivity (ECD) or flame ionization (FID) are more appropriate than a mass spectrometer.

Figure 11:
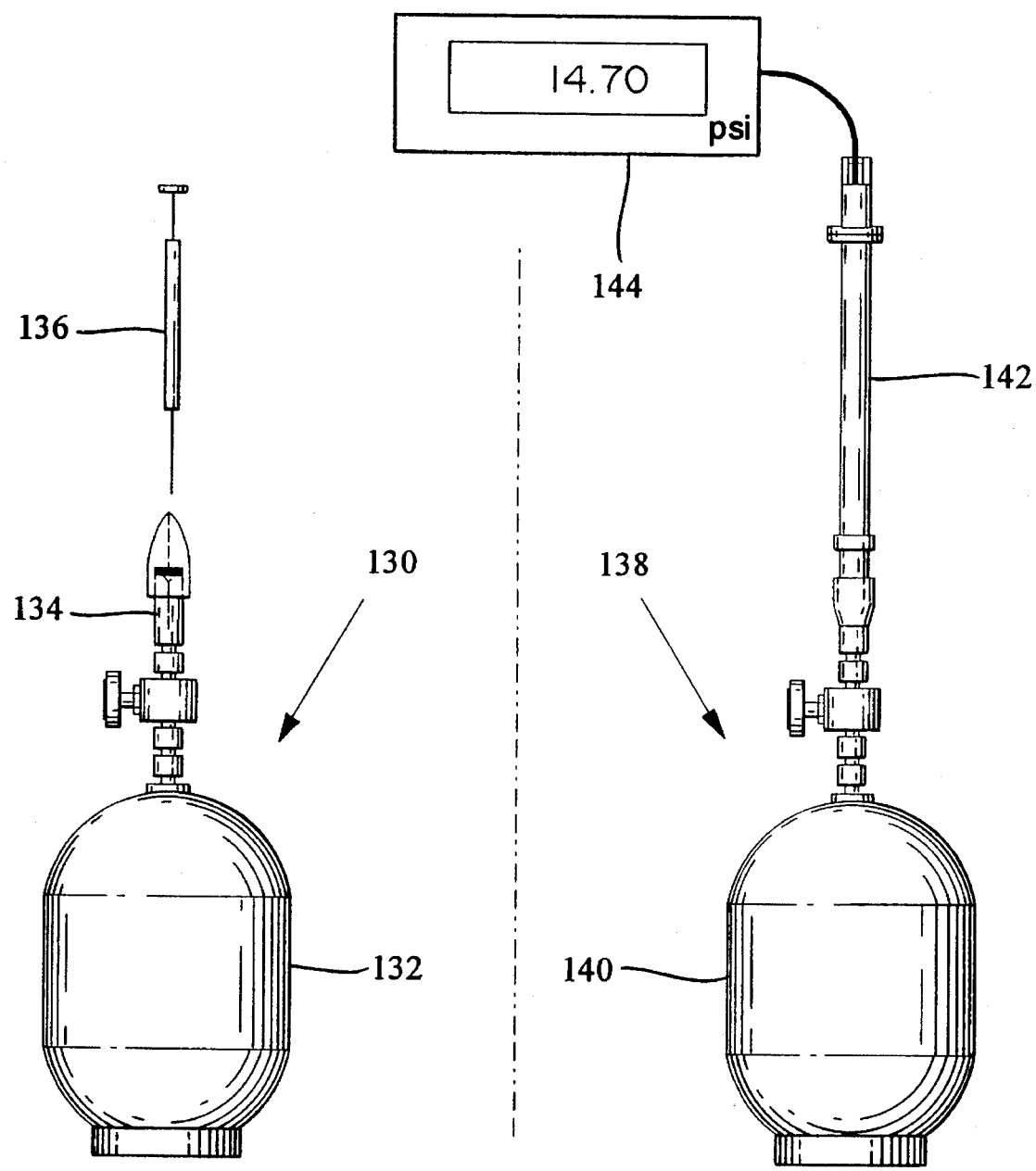
FIG. 11 is a schematic view of laboratory devices required prior to the analysis of gas samples.

With further reference to FIG. 11, there is shown a device 130 for sample management prior to laboratory analysis in which vessel 132 has a syringe adapter 134 and a gas tight syringe 136; and a device 138 having vessel 140 with a pressure transducer 142 and a calibrated reading box 144.

FIG. 11 shows the type of devices that are required before the analysis of the gas samples collected using the CSFC. First, the controller is disconnected from the vessel and replaced by a syringe adapter. Gas sample can be withdrawn inside a gas tight syringe.

Internal pressure may be monitored using a pressure transducer interfaced with a calibrated reading box as shown in FIG. 11. This procedure is required when the vessels need to be pressurized. With the analytical system presented in FIG. 10, samples are best delivered to the injector if no vacuum exist. Before they are analyzed, the samples can be mixed with purified air so that aliquots can be withdrawn for analysis. This operation dilutes the samples by a factor between 2 to 4, but with the high resolution obtained from new analytical systems, this laboratory dilution does not have a significant effect on the results obtained.

Figure 12:
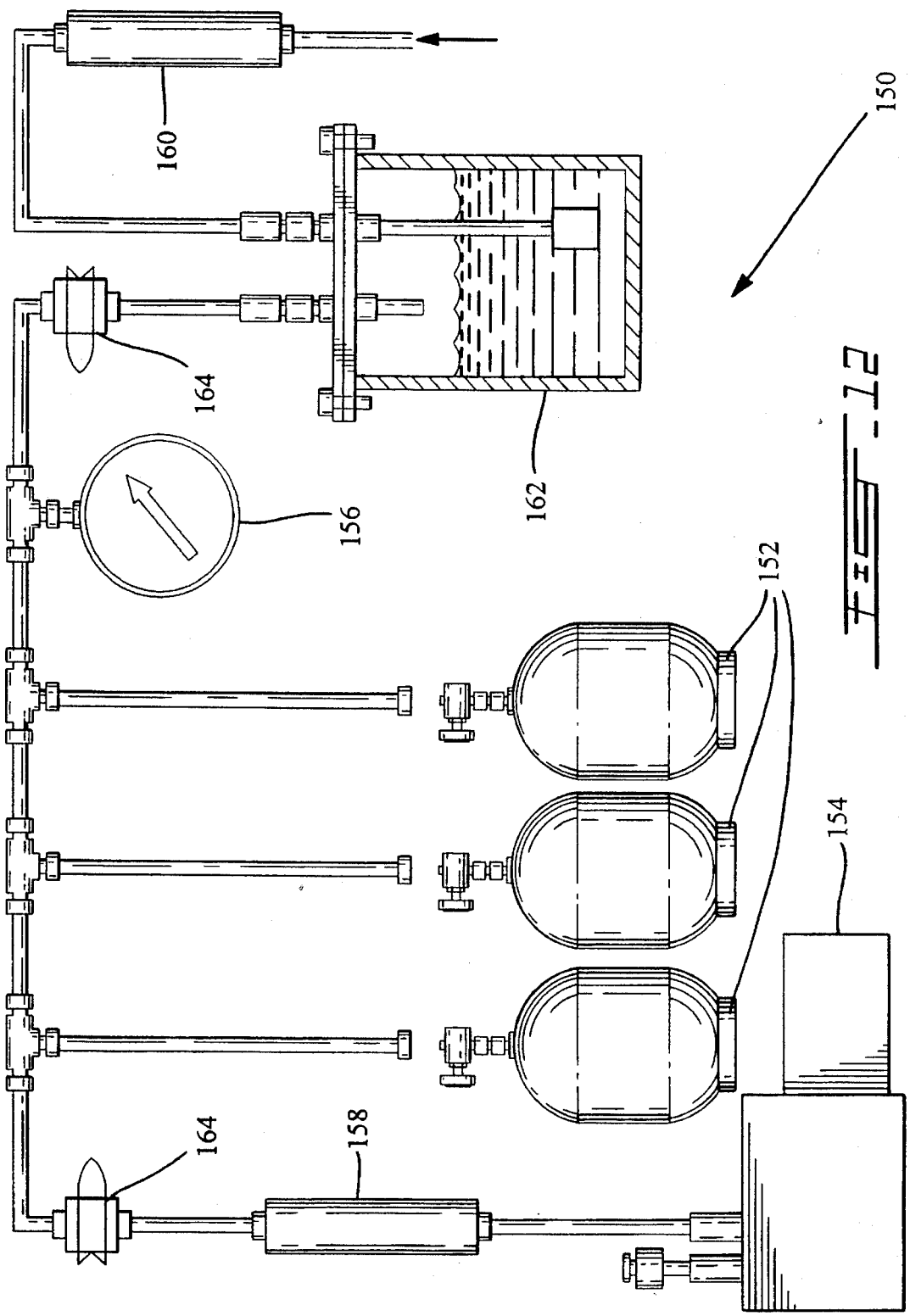
FIG. 12 is a schematic view of a laboratory system used to condition the sampling vessel tested with the present embodiment.

Compared with many of the actual sampling methodologies, the use of CSFC with evacuated sampling vessel does not require calibrations and the sampling procedures are completely independent of any power source. The CSFC can be reconditioned with purified, humidified and pressurized (10–20 psi) nitrogen, helium or air maintained at elevated temperature (100°–250° C.) and applied in reverse flow, hence it can be use more than once. The sampling vessels can also be cleaned using a reconditioning system where a source of humidified cleaned gas or a vacuum can be delivered. FIG. 12 presents a schematic view of the type of device that is required to prepare the sampling vessel for field applications and/or laboratory studies.

With further reference to FIG. 12, device 150 includes Summa canisters 152, a vacuum pulp 154, a pressure gauge 156 (–30 in Hg to 30 psi), an outlet filter 158, an inlet filter 160, a humidifying chamber 162 and manual valves 164.

This system is operated by switching the manual valves 164 to fill the canisters 152 with pure humidified gas and then to apply a vacuum given by the pump 154. These cycling steps are repeated three times or more and then the canisters 152 are kept under complete vacuum and ready to be reused.

When similar laboratory procedures can be implemented, the CSFC can provide a simple and precise method to collect inorganic gases, volatile organic gases and vapors. As compared with actual sampling methodologies using sorbent tubes, no solvents are required to analyze the passive samples collected using the CSFC.

For different air components such as particulate or reactive gases, other procedures can eventually be used. Here, the vessel would be used only to generate the motion of gas. Before entering the vessel, target contaminants would be trapped on appropriate media, (ex.: filters) installed in leak free cartridges between the CSFC and the source of vacuum. The CSFC would provide the appropriate flow rate through the intermediate collecting devices.

With the CSFC, the monitoring operation is simplified to the extent of opening and closing the valve on the evacuated vessels. It can easily be automated. Compared to existing methodologies, it does not require qualified professionals to perform the sampling tasks.

Figure 13:
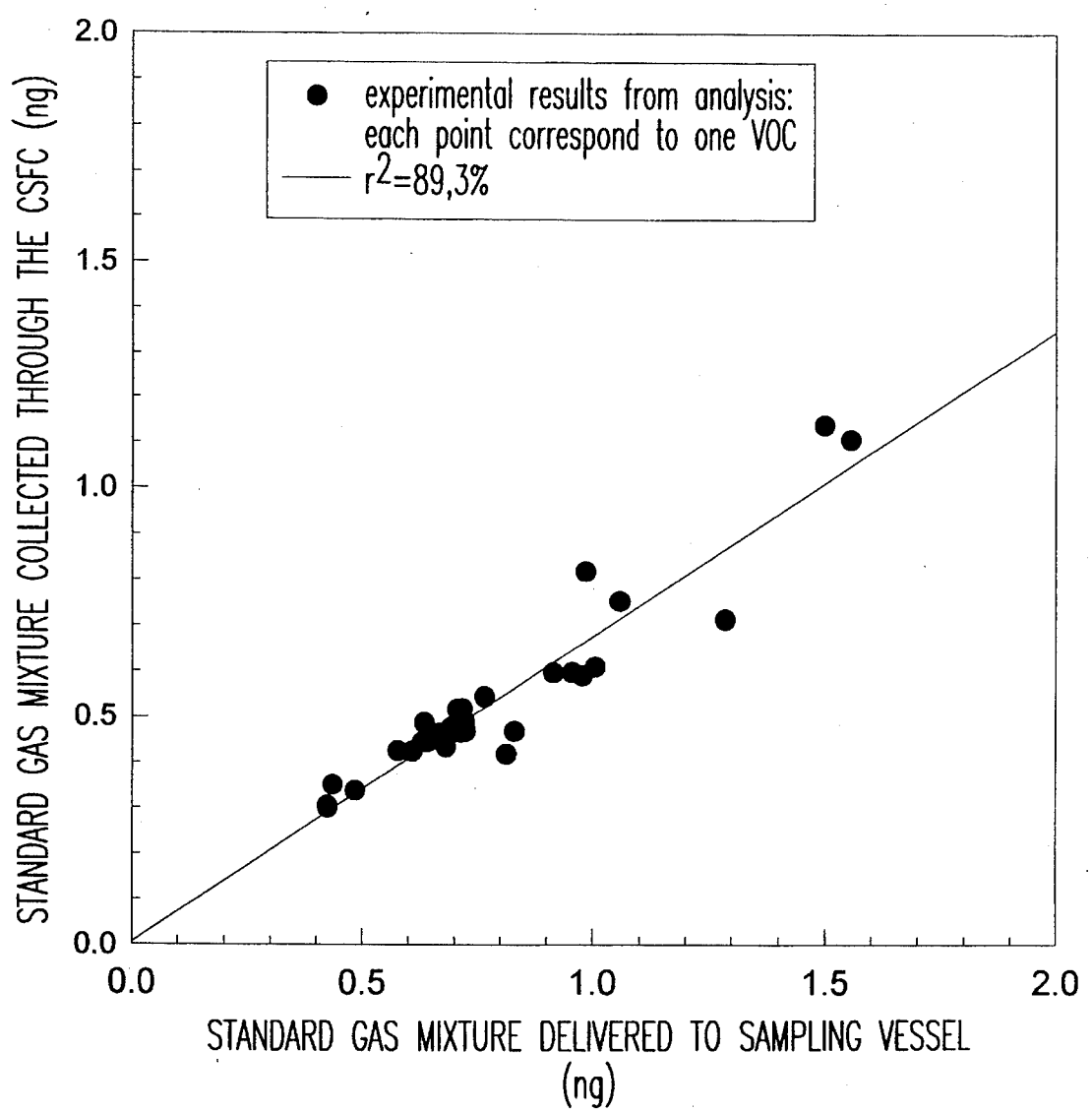
FIG. 13 is a graph showing the relationship between the levels of air pollutants delivered and collected using the invention.
Figure 14:
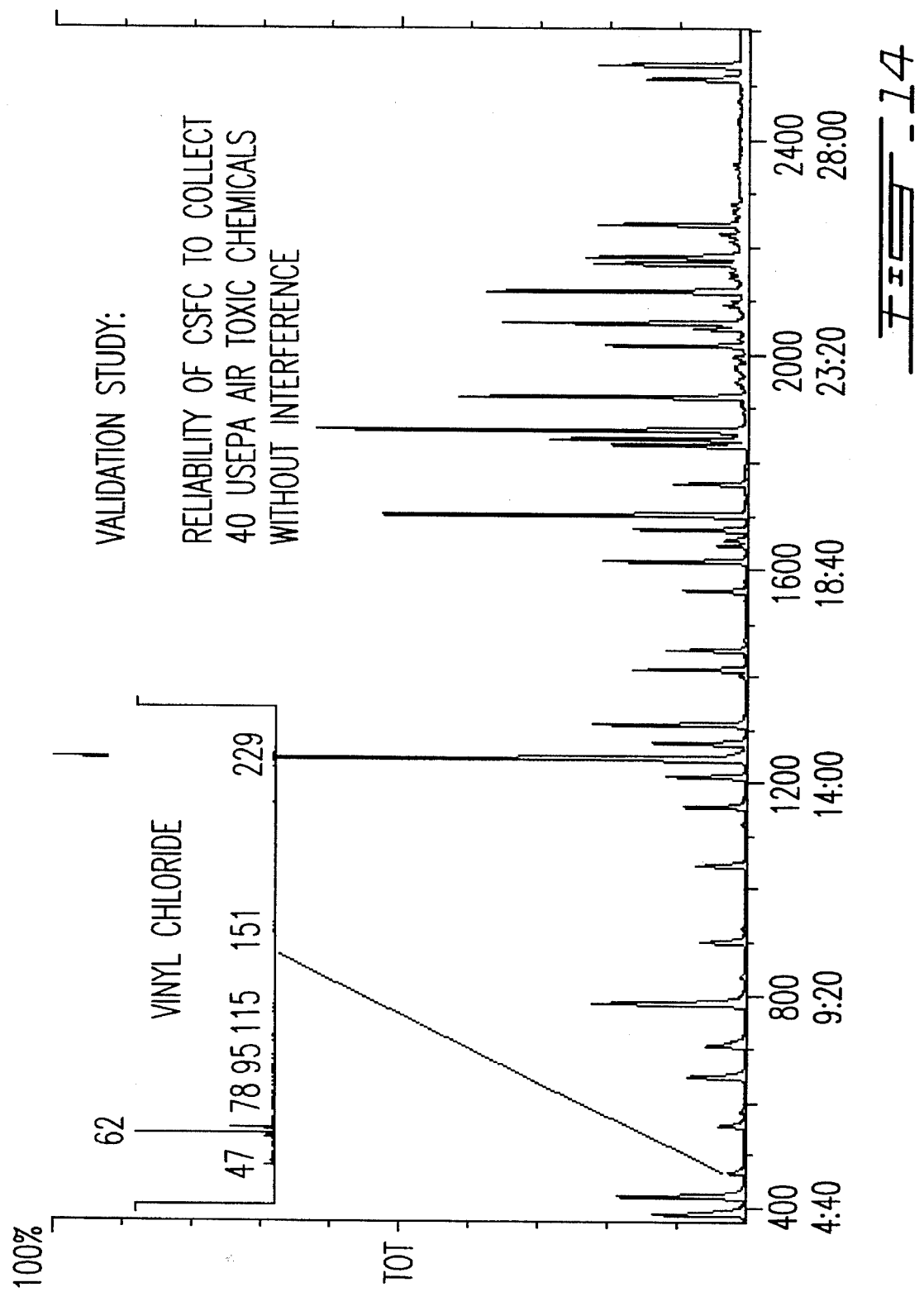
FIG. 14 is a view of a chromatogram obtained from the analysis of a gas standard mixture taken using the present invention.

Validation studies were made to demonstrate the reliability of this new atmospheric sampler. An experiment was performed where a CSFC designed to sample during 60 hour using a 500 ml evacuated Summa canister was connected using a Teflon tube directly to a 6 liter container filled at 5 psi with a standard gas mixture of 40 VOC each at 100 ppb(v). This gas mixture was transferred through the CSFC and at the end of the passive sampling period, the contents of both cylinders were analyzed in the GC/MS. Results were compared and FIG. 13 shows the relationship that was found between the levels of each VOC whether they were delivered to the sampler or collected over the long integrated sampling time. Each data point correspond to a single chemical. Globally, this experiment was conducted to prove that the CSFC does not introduce any contaminations in the gas chemistries collected for laboratory analysis. Loss of chemicals or appearance of artifacts could limit its application. According to the results presented in FIG. 13, there is no evidence that the sampling train generates interferences, considering the overall errors of the procedures (dilution, analysis). All parts of the CSFC are made of materials (e.g. deactivated fused silica and stainless steel) known to minimize the presence of active sites. FIG. 14 presents the chromatograms from the GC/MS analysis of the standard gas mixture that was collected during this experiment. The signals of every chemical of this gas matrix was correctly identified. No other chemicals (artifacts) were found. This static validation study was able to demonstrate that the capillary sampling flow controller can effectively collect samples which reproduce the nature of the atmosphere at the sampling locations.

Figure 15:
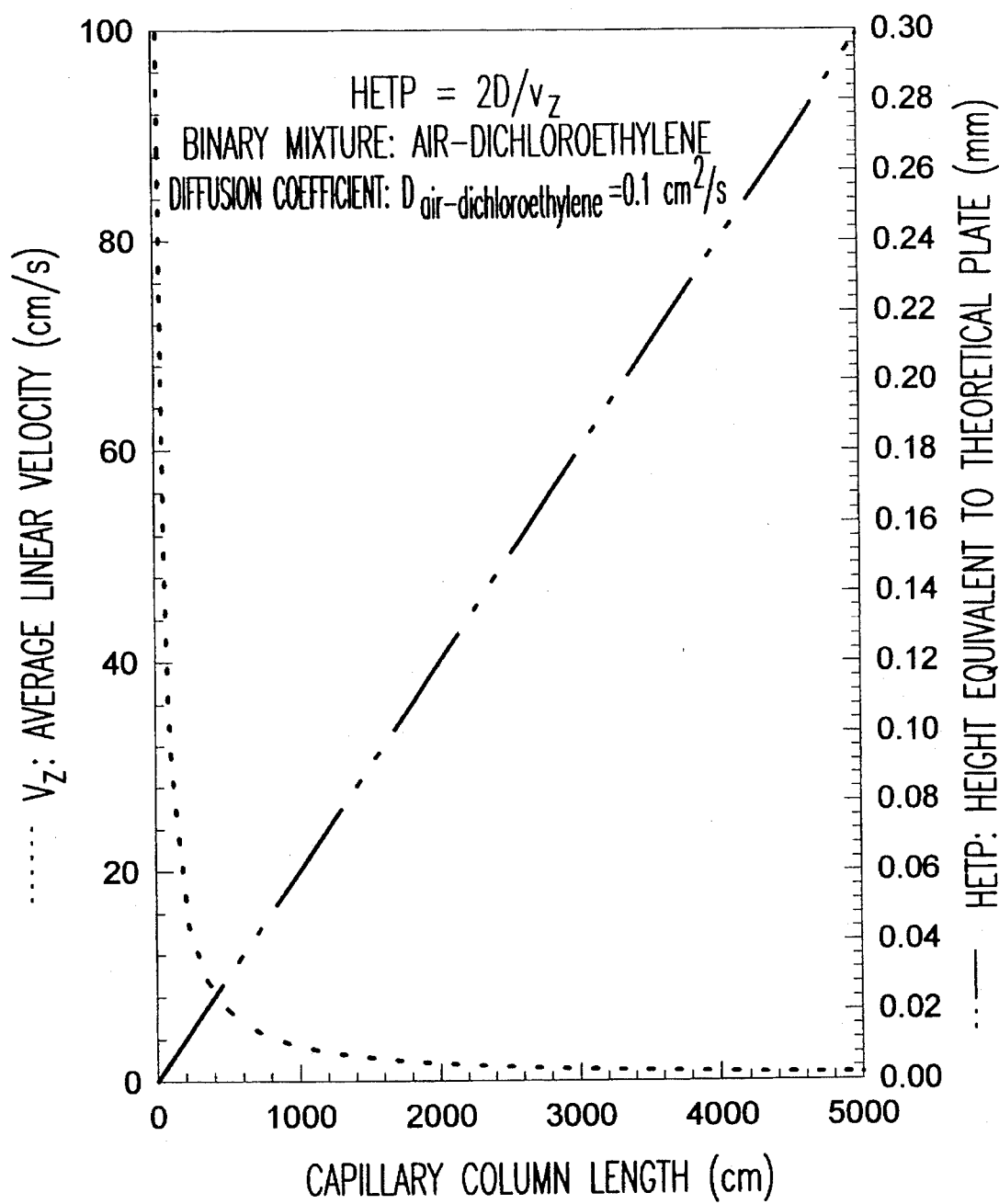
FIG. 15 is a graph showing the theoretical effect of molecular diffusion on the separation of chemicals and the validity of sampling using the present invention.
Figure 16:
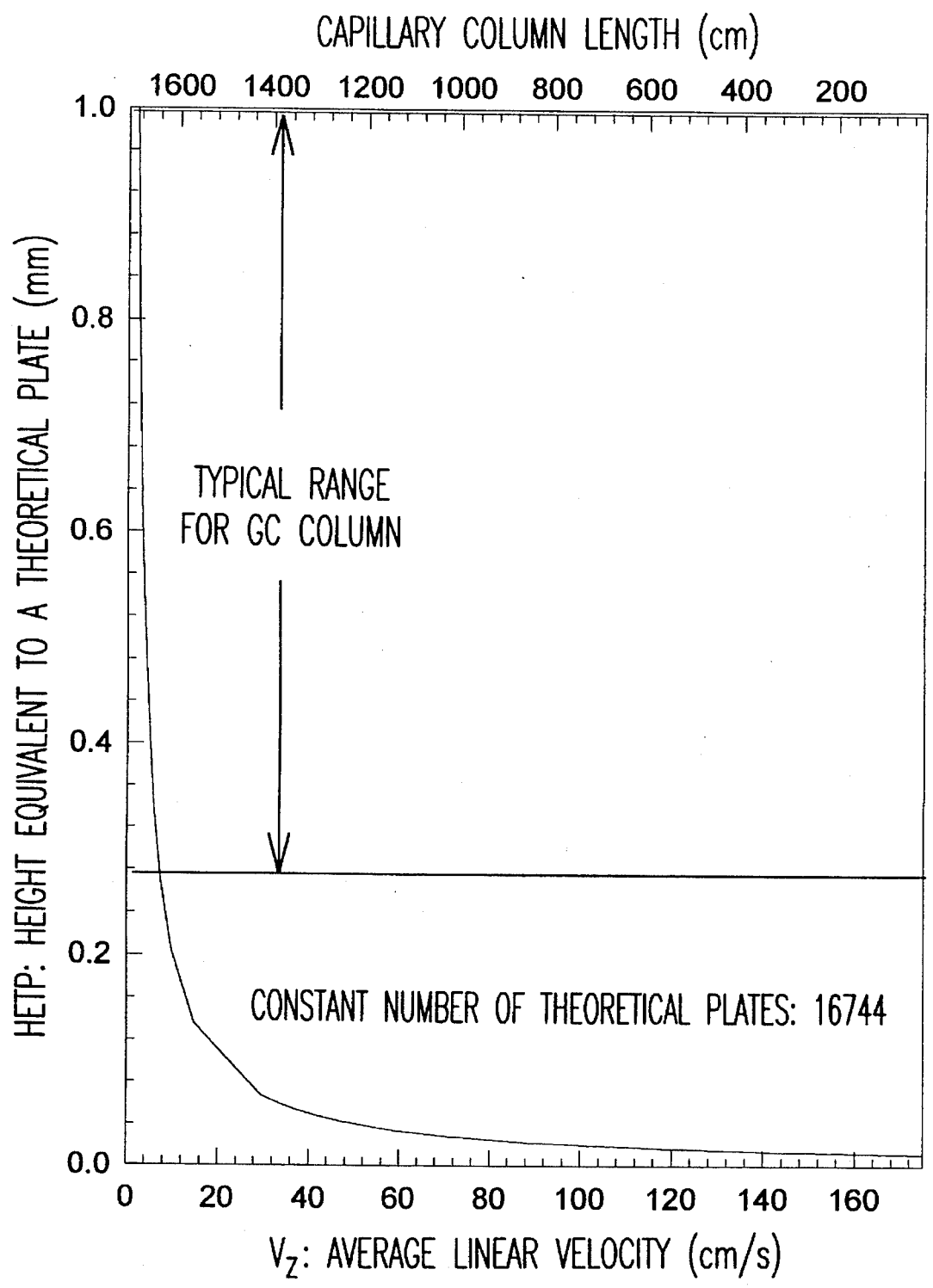
FIG. 16 is another graph showing the theoretical behavior of the present invention concerning the separation of chemicals.

The use of appropriate geometry of capillaries to control the flow rate at such low levels raised a question concerning possible separation effects inside the tube. As an analogy, the separation of a chromatographic column can be estimated using the Van Deemter equation. This relationship expresses the height equivalent to a theoretical plate which is an indication of the separation efficiency as a function of three factors that may influence the retention of molecules inside a column. This equation is written as:

$$HETP = A + \frac{B}{V_z} + Cv_z \tag{28}$$

where HETP is the height equivalent to a theoretical plate, A is the factor which represents the eddy diffusion, B is the longitudinal molecular diffusion and C is the mass transfer coefficient in the stationary phase. In the CSFC, a plain capillary without internal packing or stationary phase is used so the factors A and C are not considered. The only factor which can influence the separation is the axial molecular diffusion and based on Einstein's law of diffusion, equation (28) can be written as:

$$HETP = \frac{2D_z}{V_z} \tag{29}$$

where $D_z$ is the diffusion coefficient for a binary mixture which is measured in $cm^2/s$, and $V_z$ is the average longitudinal velocity of molecules in cm/s. The average velocity was calculated theoretically for different lengths of 0.05 mm internal diameter capillary using the cross-sectional area and the simulation results of volumetric flow rate. As an example, the tabulated diffusion coefficient for a mixture of air and dichloroethylene (0.1 $cm^2/s$) was used, and values of HETP were computed as a function of capillary length used in the design of CSFC. These results are illustrated in FIG. 15. A linear relationship between the height equivalent to theoretical plate and the length of capillary is predicted based on assumptions and considering the profile of average velocities of gas samples These data can also be expressed to show the relationship between the average velocity and the HETP. This was done to compare the results with basic theory of separation. FIG. 16 shown simulation results that were performed to study the validity of the capillary sampling flow controller. Chromatographic columns are often characterized by their number of theoretical plates. This number can be estimated using the length of column divided by the HETP. With this simple equation, calculations were performed and the number of theoretical plates was found to be independent of the length of capillary. Using a capillary of 0.05 mm in internal diameter, any lengths will introduce approximately 16,750 theoretical plates of separation for a mixture of air and dichloroethylene. Normally, GC columns need more than 200,000 plates to be efficient. From this theoretical analysis, it was shown that the level of separation which could eventually interfere in the sampling of gas chemistries is relatively low.

Figure 17:
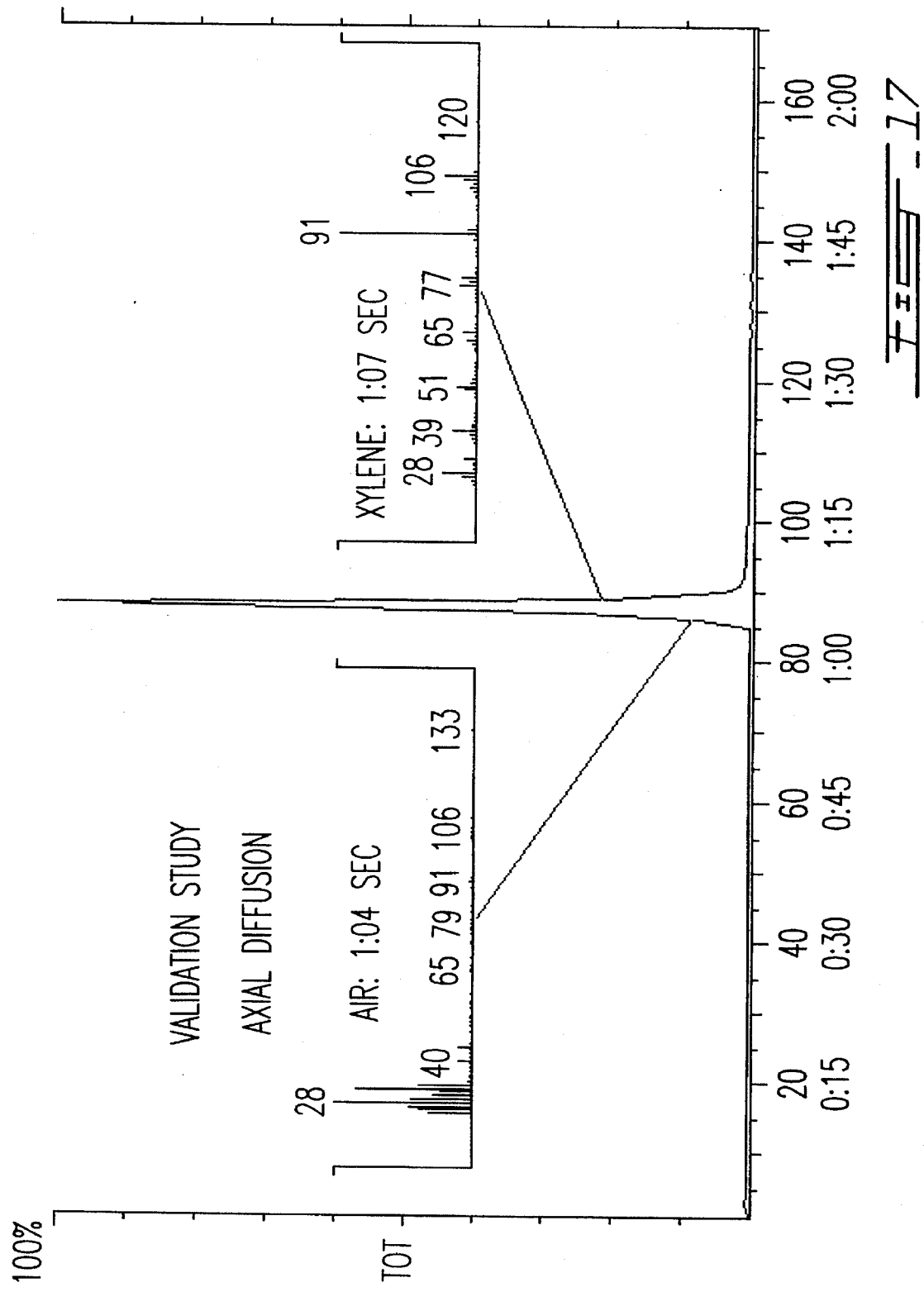
FIG. 17 is a view of a chromatogram obtained from an experiment on molecular diffusion which demonstrates the efficacy of the invention.

In order to prove that this effect is small enough to have a minor impact on the reliability of CSFC, an experiment was conducted in the laboratory using the GC/MS. The separation column inside the GC was replaced by 1 meter of deactivated fused silica column with 0,05 mm internal diameter. This capillary was directly connected between the GC injection port and the MS ion trap maintained under vacuum. The GC flow rate was reduced at atmospheric pressure and the system was kept isothermal to reproduce the conditions encountered on the field when a CSFC is used. A binary mixture of air and xylene was injected as a pulse to simulate the entry of a gas sample passing through the controller and collected inside the sampling vessel. FIG. 17 presents the chromatogram that was obtained from this experiment where 1 μl of this mixture was injected in the system with a gas tight syringe one minute after the detector and the acquisition were started. Rapidly, the mixture arrived at the detector over a time interval of less than 5 seconds. Mass spectra of air (m/e 28) was found to be more predominant in the beginning of the signal when compared with the mass spectra of xylene (m/e 91) which was higher at the end of this peak. As predicted from theoretical considerations using Van Deemter and Einstein relationships, a small separation was observed inside the capillary due to the molecular diffusion. However, these phenomena occurred over periods of seconds. This separation effect cannot have any influence on the validity of samples taken using the CSFC considering that sampling durations are extended to minutes, hours, days or months.

From every theoretical and experimental validation study performed up to date, the reliability and the applicability of the capillary sampling flow controller were demonstrated. The CSFC can fulfill many needs in air quality monitoring.

Figure 18:
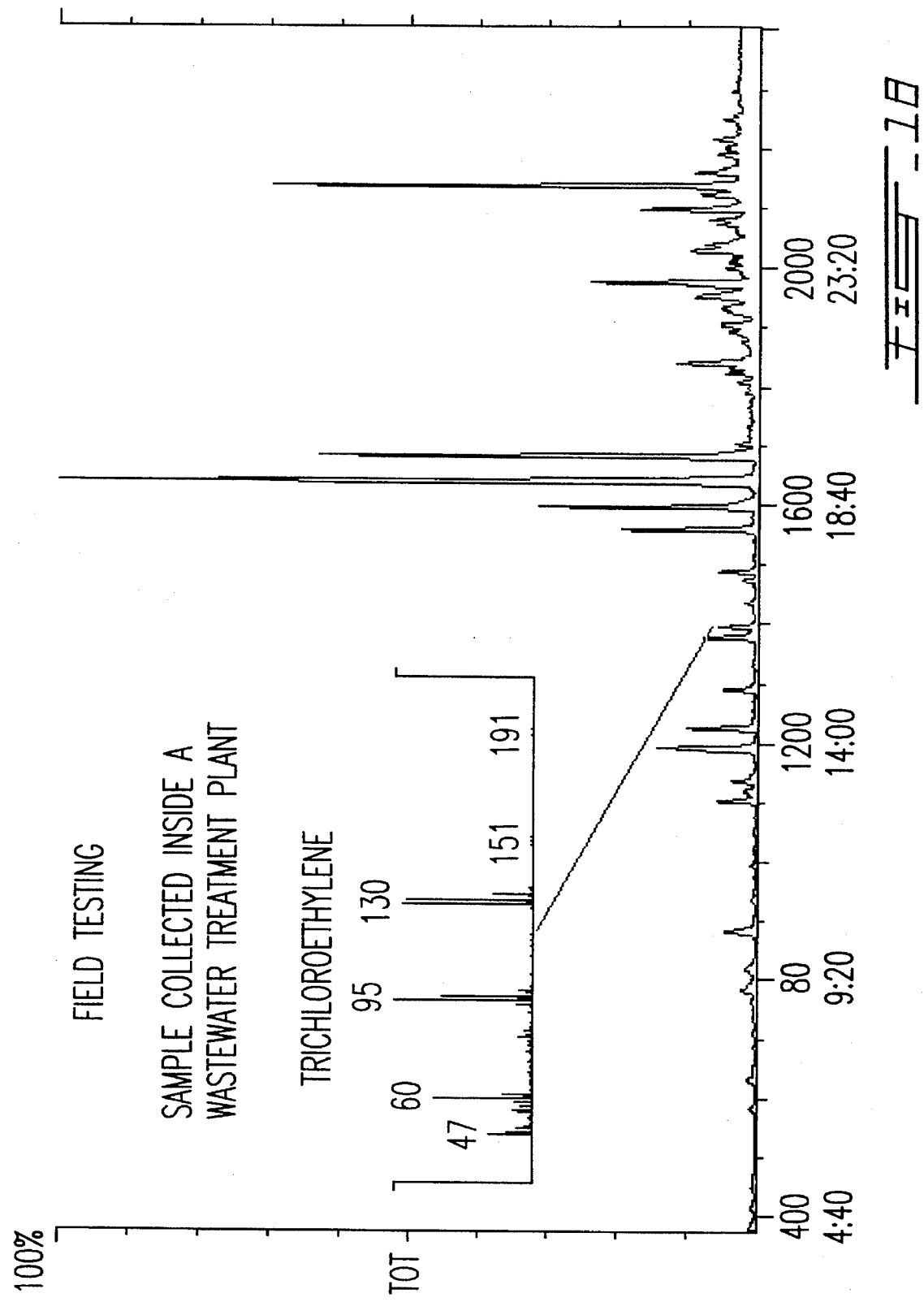
FIG. 18 is a view of a chromatogram obtained from the analysis of a field sample taken using the present invention.

Considering the possibilities offered by the novel flow controller, different configurations of CSFC have been used in the field. 21 long term stationary samples were collected outdoor around a sanitary landfill during one week periods using 1 liter and 6 liter Summa canisters. These samples were diluted with ultra pure air and analyzed through gas chromatography/mass spectrometry (GC/MS) to quantify low levels of 50 volatile organic chemicals. Methane content was also measured using gas chromatography/flame ionization detection (GC/FID). Field testings were also conducted to assess the indoor air quality inside a domestic wastewater and pulp mill treatment plant and in residences. 6 liters Summa canisters were used to sample during periods of one, two or three weeks. In all of these cases, the analysis was able to provide appropriate results which represent the mean average concentrations of airborne pollutants integrated over a long duration. FIG. 18 shows the chromatogram obtained from the analysis of one of these sample using the GC/MS.

Finally, the CSFC is now being used aboard the Russian orbital station Mir as a first trial made by the US and Russian space agencies to evaluate this invention. Ten prototypes designed to achieve a 7 days sampling time using 500 ml canister were assembled and initially tested (see FIG. 9). Four of these units were launched in Soyuz TM-23 the 21st of February 1996. They are being used inside Mir to collect air samples before and after the docking with the Priroda module. Samples will be analyzed in the laboratory when they return from space.

The capillary sampling flow controller represents an improvement in passive monitoring applied to air quality, to source characterization or to process control. Considering the simplicity and the low cost of the CSFC, combined with its ability to control the sampling period, this invention should find various other applications. It can be applied in the monitoring of many types of gas contaminants or gas components in various type of environments.

We claim:

1. A sampling assembly for the time integrated passive collection of a gas or ambient air comprising a sample vessel having a negative atmosphere, said vessel having a gas inlet and being operatively connected to a sampling flow controller comprising an elongated capillary tube having an inlet port and an outlet port with a gas flow passage therebetween, said outlet port communicating with the vessel, said capillary tube having a length and an internal diameter in accordance with the relationship $$L = \frac{K_6 R^4 t}{(e^{\frac{V_f}{K_5}} - 1)}$$

wherein
L is the length of the capillary in meters,
R is the internal radius of the capillary in meters,
$V_f$ is the final sampled volume in cubic meters,
t is the time in seconds, and
$K_5$ and $K_6$ are constants for the system in which $$K_5 = \frac{P_{atm} V_s \overline{V}}{\mathbb{R} T}$$

and $$K_6 = \frac{\pi \mathbb{R} T}{8 \mu V_s \overline{V}}$$

wherein
$\underline{P}_{atm}$ is atmospheric pressure (Pa)
V is the molar volume (m³/mole)
$\mathbb{R}$ is the gas constant (N.m/mol.k)
T is the temperature (° K.), and
$V_s$ is the volume of the vessel in cubic meters
so as to provide flow control of gas or ambient air at said gas inlet of the vessel.

2. An assembly according to claim 1, wherein said sample vessel has a volume of 50 ml to 50,000 ml, said length ranges from 5 cm to 5000 cm and said internal diameter ranges from 0.05 mm to 0.53 mm.

3. An assembly according to claim 2, wherein said inlet port is operatively connected to a filter adapted to prevent entry of particulate matter into said flow passage, and a pressure measuring device is operatively connected between said outlet port and said gas inlet.

4. An assembly according to claim 1, wherein said capillary tube is a deactivated fused silica column.

5. An assembly according to claim 1, wherein said capillary tube is enclosed within a protective housing.

6. An assembly according to claim 5, wherein said housing contains packing material for absorbing vibrations and preventing breakage of the tube during transportation or handling.

7. An assembly according to claim 1, further including mounting means for mounting said vessel on a support adapted to be worn by a person, said vessel being of a size and weight suitable for being carried by the person on the support; and means for mounting the inlet port adjacent the breathing zone of the person.

8. A process of time integrated sampling for the analysis of a gas comprising the steps of:

introducing a gas sample at a substantially constant flow rate into an evacuated vessel along an elongated capillary tube having an inlet port and an outlet port with a flow passage therebetween, said capillary tube being of a length and internal diameter in accordance with the relationship $$L = \frac{K_6 R^4 t}{(e^{\frac{V_f}{K_5}} - 1)}$$

wherein
L is the length of the capillary in meters,
R is the internal radius of the capillary in meters,
$V_f$ is the final sampled volume in cubic meters,
t is the time in seconds, and
$K_5$ and $K_6$ are constants for the system in which $$K_5 = \frac{P_{atm} V_s \overline{V}}{\mathbb{R} T}$$

and $$K_6 = \frac{\pi \mathbb{R} T}{8 \mu V_s \overline{V}}$$

wherein
$\underline{P}_{atm}$ is atmospheric pressure (Pa)
V is the molar volume (m³/mole)
$\mathbb{R}$ is the gas constant (N.m/mol.k)
T is the temperature (° K.), and
$V_s$ is the volume of the vessel (m³)
so as to provide flow control at said outlet port and a predetermined sampling duration.

9. A process according to claim 8, wherein said evacuated vessel has a volume of 50 ml to 50,000 ml, said length ranges from 5 cm to 5000 cm and said internal diameter ranges from 0.05 mm to 0.53 mm.

10. A process according to claim 8, wherein said inlet port is operatively connected to a filter, and including a step of filtering particulate matter from the gas sample entering said inlet port to prevent entry of said particulate matter into said flow passage, and further including a step of monitoring pressure of the gas developed in said vessel, from said gas sample.

11. A process according to claim 8, wherein said capillary tube is a deactivated fused silica column.

12. A process according to claim 8, wherein said gas is ambient air.

13. A sampling flow controller for time integrated flow of gas or ambient air during collection comprising, in combination:

an elongated capillary tube having an inlet port and an outlet port with a gas flow passage therebetween, means for communicating said outlet port with a sample vessel adapted to be held under a negative pressure, and a filter operatively connected to said inlet port for prevention of entry of particulate matter into said flow passage, said capillary tube having a length and an internal diameter in accordance with the relationship $$L = \frac{K_6 R^4 t}{(e^{\frac{V_f}{K_5}} - 1)}$$

wherein
L is the length of the capillary in meters,
R is the internal radius of the capillary in meters,
$V_f$ is the final sampled volume in cubic meters,
t is the time in seconds, and
$K_5$ and $K_6$ are constants for the system in which $$K_5 = \frac{P_{atm} V_s \overline{V}}{\mathbb{R} T}$$

and $$K_6 = \frac{\pi \mathbb{R} T}{8 \mu V_s \overline{V}}$$

wherein

P$_{atm}$ is atmospheric pressure (Pa)

V is the molar volume (m$^3$/mole)

$\mathbb{R}$ is the gas constant (N.m/mol.k)

T is the temperature (° K.), and

V$_s$ is the volume of the vessel (m$^3$), so as to provide flow control of gas or ambient air at said outlet port.

14. A controller according to claim 13, wherein the length and internal diameter are selected in accordance with the relationship $$L = \frac{K_6 R^4 t}{(e^{\frac{V_f}{K_5}} - 1)}$$

wherein

L is the length of the capillary in meters,

R is the internal radius of the capillary in meters,

V$_f$ is the final sampled volume in cubic meters, t is the time in seconds, and K$_5$ and K$_6$ are constants for the system in which $$K_5 = \frac{P_{atm} V_s \overline{V}}{\mathbb{R} T}$$

and $$K_6 = \frac{\pi \mathbb{R} T}{8 \mu V_s \overline{V}}$$

wherein

P$_{atm}$ is atmospheric pressure (Pa)

V is the molar volume (m$^3$/mole)

$\mathbb{R}$ is the gas constant (N.m/mol.k)

T is the temperature (° K.), and

V$_s$ is the volume of the vessel (m$^3$).

15. A controller according to claim 14, wherein said length ranges from 5 cm to 5000 cm and said internal diameter ranges from 0.05 to 0.53 mm.

16. A controller according to claim 14, wherein said capillary tube is enclosed within a protective housing containing packing material for absorbing vibrations and preventing breakage of the tube during transportation or handling, and including an elongate sampling line connecting said inlet port and said filter.

17. A controller according to claim 14, further including a pressure measuring device operatively connected to said outlet port.

* * * * *